US012070075B2

United States Patent
Takeuchi et al.

(10) Patent No.: US 12,070,075 B2
(45) Date of Patent: Aug. 27, 2024

(54) POWER SUPPLY ASSEMBLY, NON-COMBUSTION-TYPE FLAVOR INHALER, AND NON-COMBUSTION-TYPE FLAVOR INHALATION SYSTEM

(71) Applicant: JAPAN TOBACCO INC., Tokyo (JP)

(72) Inventors: Manabu Takeuchi, Tokyo (JP); Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 637 days.

(21) Appl. No.: 16/014,398

(22) Filed: Jun. 21, 2018

(65) Prior Publication Data

US 2018/0296779 A1    Oct. 18, 2018

Related U.S. Application Data

(63) Continuation of application No. PCT/JP2015/085879, filed on Dec. 22, 2015.

(51) Int. Cl.
*A24F 40/53*    (2020.01)
*A24F 40/40*    (2020.01)
(Continued)

(52) U.S. Cl.
CPC .............. *A24F 40/53* (2020.01); *A24F 40/40* (2020.01); *A24F 40/90* (2020.01); *A24F 40/95* (2020.01);
(Continued)

(58) Field of Classification Search
CPC .......... A24F 40/90; A24F 40/95; A61M 15/06
See application file for complete search history.

(56) References Cited

U.S. PATENT DOCUMENTS 5,661,780 A    8/1997    Yamamoto et al.
9,655,383 B2   5/2017    Holzherr et al.
(Continued)

FOREIGN PATENT DOCUMENTS

CN    103989255 A    8/2014
CN    204579890 U    8/2015
(Continued)

OTHER PUBLICATIONS

International Search Report (PCT/ISA/210) issued in PCT/JP2015/085879, mailed on Mar. 22, 2016.
(Continued)

*Primary Examiner* — Philip Y Louie
*Assistant Examiner* — Sonny V Nguyen
(74) *Attorney, Agent, or Firm* — Birch, Stewart, Kolasch & Birch, LLP

(57) ABSTRACT

A non-combustion-type flavor inhaler includes: an atomization assembly including an atomizer configured to atomize an aerosol source without combustion; and a power supply assembly including a power supply for supplying power to the atomizer. The power supply assembly includes: paired electrodes for electrical connection with the atomizer; and a first electrode and a second electrode electrically connected with the power supply. At least one of the first electrode and the second electrode is electrically connectable to a charger for charging the power supply. The non-combustion-type flavor inhaler is provided with a control circuit configured to detect a predetermined current in an opposite direction to a direction of a current flowing through the first electrode or the second electrode when the charger charges the power supply.

22 Claims, 20 Drawing Sheets

(51) Int. Cl.
    *A24F 40/90*     (2020.01)
    *A24F 40/95*     (2020.01)
    *A61M 11/04*     (2006.01)
    *A61M 15/00*     (2006.01)
    *A61M 15/06*     (2006.01)
    *G05F 1/66*     (2006.01)
    *A24F 40/10*     (2020.01)
    *A24F 40/20*     (2020.01)
    *H05B 1/02*     (2006.01)

(52) U.S. Cl.
CPC ...... *A61M 11/042* (2014.02); *A61M 15/0085* (2013.01); *A61M 15/06* (2013.01); *G05F 1/66* (2013.01); *A24F 40/10* (2020.01); *A24F 40/20* (2020.01); *A61M 2205/3653* (2013.01); *H05B 1/0244* (2013.01)

(56) References Cited

U.S. PATENT DOCUMENTS

| | | | |
|---|---|---|---|
| 2009/0128159 A1* | 5/2009 | Nakatsuji | G01R 31/52 324/433 |
| 2014/0299137 A1 | 10/2014 | Kieckbusch et al. | |
| 2015/0020831 A1* | 1/2015 | Weigensberg | A24F 47/008 131/329 |
| 2015/0020832 A1* | 1/2015 | Greim | A24F 47/008 131/329 |
| 2015/0043117 A1* | 2/2015 | Xiang | A24F 40/90 361/91.5 |
| 2016/0278433 A1 | 9/2016 | Xiang | |
| 2017/0207499 A1* | 7/2017 | Leadley | A24F 40/95 |
| 2017/0303597 A1* | 10/2017 | Tsui | A24F 40/90 |
| 2018/0027878 A1* | 2/2018 | Dendy | H01M 10/46 |
| 2018/0198297 A1* | 7/2018 | Grzan | H02J 7/0042 |
| 2022/0046997 A1* | 2/2022 | Atkins | A24F 40/51 |
| 2022/0077698 A1* | 3/2022 | Aradachi | H02J 7/0047 |

FOREIGN PATENT DOCUMENTS

| | | |
|---|---|---|
| JP | 9-27836 A | 1/1997 |
| JP | 2011-87569 A | 5/2011 |
| JP | 2015-534458 A | 12/2015 |
| WO | WO 2013/093695 A1 | 6/2013 |
| WO | WO 2014/150704 A2 | 9/2014 |
| WO | WO 2015/023996 A2 | 2/2015 |
| WO | WO 2015/027547 A1 | 3/2015 |
| WO | WO 2015/150759 A1 | 10/2015 |

OTHER PUBLICATIONS

Taiwan Office Action for application No. 105137036 mailed Dec. 27, 2017.
Canadian Office Action, dated May 3, 2019, for Canadian Application No. 3,009,050.
Extended European Search Report, dated May 24, 2019, for European Application No. 15911306.7.
Chinese Office Action and Search Report for Chinese Application No. 201580085476.2, dated Mar. 31, 2020, with an English translation.

* cited by examiner

POWER SUPPLY ASSEMBLY, NON-COMBUSTION-TYPE FLAVOR INHALER, AND NON-COMBUSTION-TYPE FLAVOR INHALATION SYSTEM

CROSS REFERENCE TO RELATED APPLICATIONS

This application is a Continuation of PCT International Application No. PCT/JP2015/085879, filed on Dec. 22, 2015, which is hereby incorporated by reference into the present application.

TECHNICAL FIELD

The present invention relates to a power supply assembly including a power supply for supplying power to an atomizer that atomizes an aerosol source without combustion, a non-combustion-type flavor inhaler including the power supply assembly, and a non-combustion-type flavor inhalation system including the non-combustion-type flavor inhaler.

BACKGROUND ART

A non-combustion-type flavor inhaler (electric smoking article) that provides a flavor without combustion of a flavor source, such as tobacco, has been proposed instead of a cigarette. Patent Literature 1 discloses an electric smoking article having an aerosol generation source. The electric smoking article includes: a liquid storage that stores a liquid; a heater that vaporizes the liquid sent from the liquid storage; and a power supply that supplies power to the heater. Patent Literature 1 discloses a technique of preventing the electric smoking article from being used by an unauthorized user, with application of a user authentication technique.

CITATION LIST

Patent Literature

Patent Literature 1: WO 2014/150704 A

SUMMARY

A first feature is a non-combustion-type flavor inhaler including: an atomization assembly including an atomizer configured to atomize an aerosol source without combustion; and a power supply assembly including a power supply for supplying power to the atomizer. The power supply assembly includes: paired electrodes for electrical connection with the atomizer; and a first electrode and a second electrode electrically connected with the power supply. At least one of the first electrode and the second electrode is electrically connectable to a charger for charging the power supply. The non-combustion-type flavor inhaler is provided with a control circuit configured to detect a predetermined current in an opposite direction to a direction of a current flowing through the first electrode or the second electrode when the charger charges the power supply.

The second feature is the non-combustion-type flavor inhaler according to the first feature, wherein the power supply is configured to generate the predetermined current to be supplied to the control circuit.

The third feature is the non-combustion-type flavor inhaler according to the first feature or the second feature, wherein the power supply assembly includes a first case housing the power supply, the first case including first paired electrodes being the paired electrodes, the atomization assembly includes a second case housing the atomizer, the second case including second paired electrodes, the second case being detachably attachable to the first case, and the first paired electrodes and the second paired electrodes are configured to electrically connect together when the first paired electrodes and the second paired electrodes are in contact with each other.

The fourth feature is the non-combustion-type flavor inhaler according to the third feature, wherein at least one of the first case and the second case includes an engagement for engaging the first case and the second case together.

The fifth feature is the non-combustion-type flavor inhaler according to the third feature or the fourth feature, wherein, with the first paired electrodes and the second paired electrodes electrically connected together, the first electrode and the second electrode are disposed at positions at which an external element different from constituent elements of the non-combustion-type flavor inhaler enables the first electrode and the second electrode to be in conduction.

The sixth feature is the non-combustion-type flavor inhaler according to any one of the third feature to the fifth feature, wherein, with the first paired electrodes and the second paired electrodes electrically connected together, each of the first electrode and the second electrode have a portion exposed on a surface of the first case.

The seventh feature is the non-combustion-type flavor inhaler according to any one of the third feature to the fifth feature, wherein, with the first paired electrodes and the second paired electrodes electrically connected together, the first paired electrodes are disposed at positions at which conduction of an external element different from constituent elements of the non-combustion-type flavor inhaler, is not allowed between the first paired electrodes.

The eighth feature is the non-combustion-type flavor inhaler according to the seventh feature, wherein, with the first paired electrodes and the second paired electrodes electrically connected together, at least one of the first paired electrodes is not exposed on a surface of the non-combustion-type flavor inhaler.

The ninth feature is the non-combustion-type flavor inhaler according to the sixth feature, wherein an exposed portion of the first electrode and an exposed portion of the second electrode are disposed on faces facing mutually different directions in the first case.

The tenth feature is the non-combustion-type flavor inhaler according to the sixth feature, wherein an exposed portion of the first electrode and an exposed portion of the second electrode are disposed on faces facing identical directions in the first case, and a difference in level is provided between an end face of the exposed portion of the first electrode and an end face of the exposed portion of the second electrode.

The eleventh feature is the non-combustion-type flavor inhaler according to any one of the first feature to the tenth feature, wherein both of the first electrode and the second electrode are electrically connectable to the charger for charging the power supply, and the power supply is configured to be charged by the charger through the first electrode and the second electrode.

The twelfth feature is the non-combustion-type flavor inhaler according to any one of the first feature to the eleventh feature, wherein the control circuit includes: a detector configured to detect the predetermined current; and a rectifying element configured to prevent a charging current from flowing in the detector.

The thirteenth feature is the non-combustion-type flavor inhaler according to the twelfth feature, wherein the rectifying element includes an anode and a cathode, the anode is electrically connected with the detector, and the cathode is electrically connected with an electrode positive during the charging by the charger, among the first electrode and the second electrode.

The fourteenth feature is the non-combustion-type flavor inhaler according to any one of the first feature to the tenth feature, wherein the power supply is configured to be charged by the charger through one of the first electrode and the second electrode.

The fifteenth feature is the non-combustion-type flavor inhaler according to any one of the first feature to the tenth feature, wherein the power supply assembly includes a third electrode different from the first electrode and the second electrode, and the charging current is configured to be supplied from the charger to the power supply through the third electrode and only one of the first electrode and the second electrode.

The sixteenth feature is the non-combustion-type flavor inhaler according to the fifteenth feature, wherein an electrode that does not contribute to supply of the charging current supplied from the charger to the power supply, among the first electrode and the second electrode is: provided at a position at which the electrode is physically out of contact with the charger; physically in contact with the charger through an insulator preventing electrical connection with the charger; or electrically connected with the charger and does not contribute to the supply of the charging current from the charger to the power supply.

The seventeenth feature is the non-combustion-type flavor inhaler according to any one of the first feature to the sixteenth feature, wherein the control circuit is configured to control a power from the power supply to the atomizer.

The eighteenth feature is the non-combustion-type flavor inhaler according to the seventeenth feature, wherein the controller is configured to perform a predetermined control in response to a length of a period of the predetermined current detected by the control circuit.

The nineteenth feature is the non-combustion-type flavor inhaler according to the seventeenth feature or the eighteenth feature, wherein the control circuit is configured to perform a predetermined control when the control circuit has detected the predetermined current a plurality of times within a predetermined period.

The twentieth feature is the non-combustion-type flavor inhaler according to the eighteenth feature or the nineteenth feature, wherein the control circuit cancels the predetermined control when the control circuit has continuously detected the predetermined current for a predetermined time or more.

The twenty-first feature is the non-combustion-type flavor inhaler according to any one of the seventeenth feature to the twentieth feature, wherein, the control circuit is configured to perform a predetermined control based on a level of an electric resistance value of the external element when the control circuit detects the predetermined current generated by an external element different from constituent elements of the non-combustion-type flavor inhaler, The twenty-second feature is the non-combustion-type flavor inhaler according to any one of the seventeenth feature to the twenty-second feature, wherein the control circuit detects whether the power supply is being charged, and the control circuit does not perform a predetermined control regardless of a detected result of the predetermined current when detecting the charging of the power supply.

A twenty-third feature is a non-combustion-type flavor inhalation system comprising: the non-combustion-type flavor inhaler according to any one of the first feature to the twenty-second feature; and a charger detachably attachable to the non-combustion-type flavor inhaler, the charger being capable of supplying a charging current to the non-combustion-type flavor inhaler.

The twenty-fourth feature is the non-combustion-type flavor inhalation system according to the twenty-third feature, wherein the charger includes third paired electrodes for electrical connection between the charger and the non-combustion-type flavor inhaler, the third paired electrodes are electrically connected with the first electrode and the second electrode when the charger and the non-combustion-type flavor inhaler are attached to each other, and the predetermined current to the control circuit is configured to be supplied by a conduction between the electrodes included in the third paired electrodes.

The twenty-fifth feature is the non-combustion-type flavor inhalation system according to the twenty-fourth feature, wherein the charger includes switching means capable of switching a state between the electrodes included in the third paired electrodes, between a conduction state and a non-conduction state.

A twenty-sixth feature is a power supply assembly comprising: a power supply for supplying power to an atomizer configured to atomize an aerosol source without combustion; paired electrodes for electrical connection with the atomizer; and a first electrode and a second electrode electrically connected with the power supply, wherein at least one of the first electrode and the second electrode is electrically connectable to a charger for charging the power supply; and a controller configured to detect a predetermined current in an opposite direction to a direction of a current flowing through the first electrode or the second electrode when the charger charges the power supply.

According to one aspect, the first electrode and the second electrode are not for electrical connection with the atomization assembly. The first electrode and the second electrode may be disposed so that the first electrode and the second electrode cannot be electrically connected with the paired electrodes provided to the atomization assembly. According to a different aspect, the paired electrodes for electrical connection with the atomizer, may be electrically connectable to the charger.

According to one aspect, the charger includes a secondary battery, and the secondary battery may be electrically connectable to an external power supply, such as a wall outlet. According to one aspect, the non-combustion-type flavor inhaler may include display means for notifying a user that the control circuit has detected the predetermined current, the display means being electrically connected with the control circuit.

DESCRIPTION OF EMBODIMENTS

Embodiments will be described below. Note that the same or similar parts are denoted with the same or similar reference signs in the descriptions of the drawings below. It should be noted that the drawings each are schematic and each ratio in dimensions may be different from an actual ratio.

Therefore, for example, specific dimensions should be judged in consideration of the following descriptions. Needless to say, parts in which the relationship or ratio in dimensions varies between the mutual drawings, may be included.

[Outline of Disclosure]

The user authentication technique with fingerprint authentication has been known as in the electric smoking article mentioned in background art. The present invention provides a power supply assembly, a non-combustion-type flavor inhaler, and a non-combustion-type flavor inhalation system that are capable of performing user authentication and selection between operation modes with a different mechanism from the user authentication technique with the fingerprint authentication.

A non-combustion-type flavor inhaler according to the outline of the disclosure including: an atomization assembly including an atomizer configured to atomize an aerosol source without combustion; and a power supply assembly including a power supply for supplying power to the atomizer. The power supply assembly includes: paired electrodes for electrical connection with the atomizer; and a first electrode and a second electrode electrically connected with the power supply, at least one of the first electrode and the second electrode being electrically connectable to a charger for charging the power supply. The power supply assembly is provided with a control circuit configured to detect a predetermined current in an opposite direction to a direction of a current flowing through the first electrode or the second electrode when the charger charges the power supply.

A power supply assembly according to the outline of the disclosure including: a power supply for supplying power to an atomizer configured to atomize an aerosol source without combustion; paired electrodes for electrical connection with the atomizer; a first electrode and a second electrode electrically connected with the power supply, at least one of the first electrode and the second electrode being electrically connectable to a charger for charging the power supply; and a controller configured to detect a predetermined current in an opposite direction to a direction of a current flowing through the first electrode or the second electrode when the charger charges the power supply.

According to the outline of the disclosure, at least one of the first electrode and the second electrode for detection of conduction for performance of, for example, user authentication or selection between operation modes, can be used as an electrode for charging the power supply of the power supply assembly.

First Embodiment (Non-Combustion-Type Flavor Inhaler)

Figure 1:
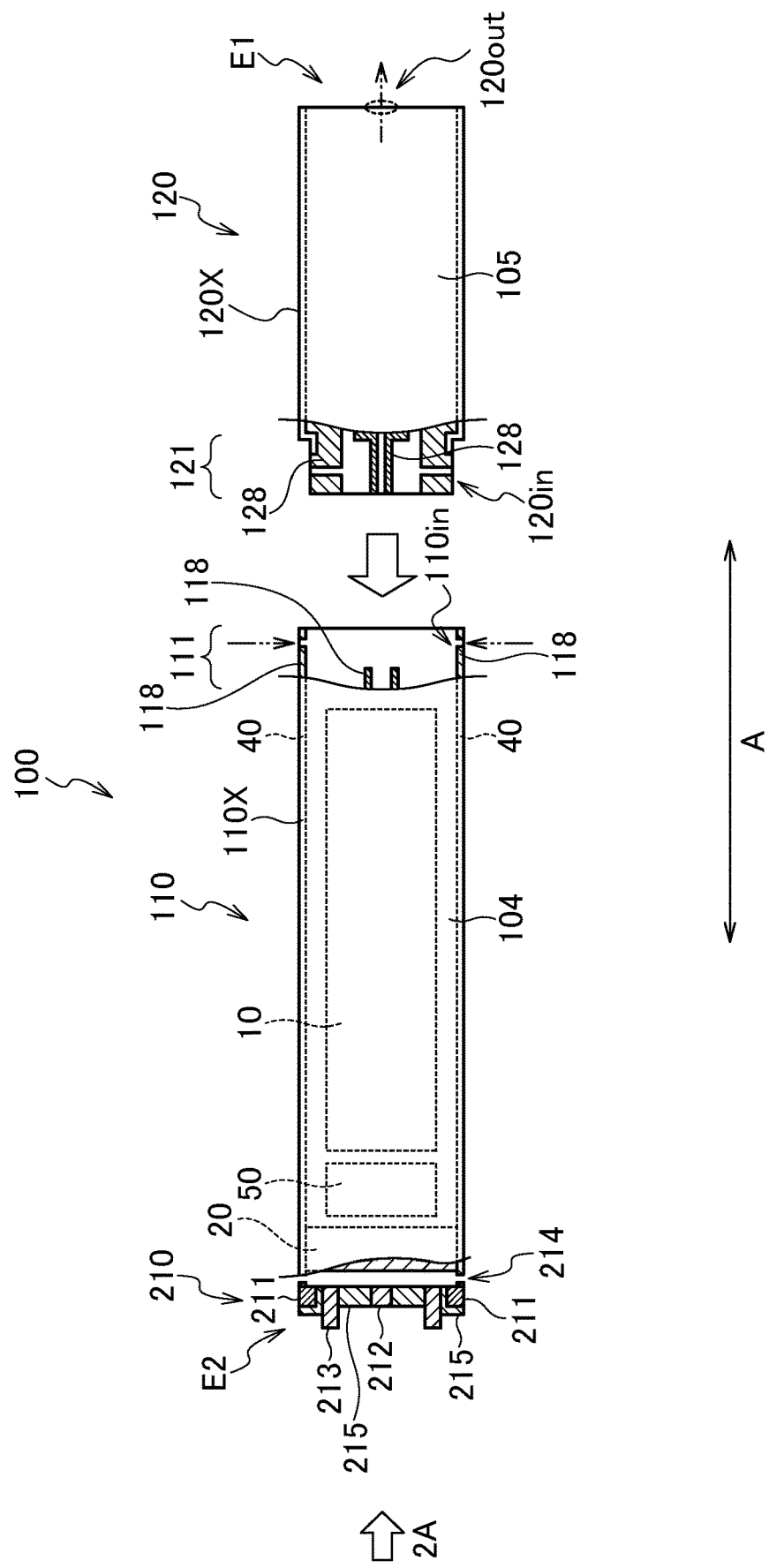
FIG. 1 is a view of a non-combustion-type flavor inhaler according to a first embodiment.
Figure 2:
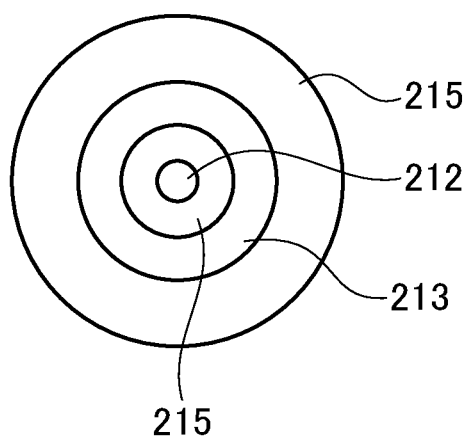
FIG. 2 is a plan view of a power supply assembly viewed in the direction of an arrow 2A of FIG. 1.
Figure 3:
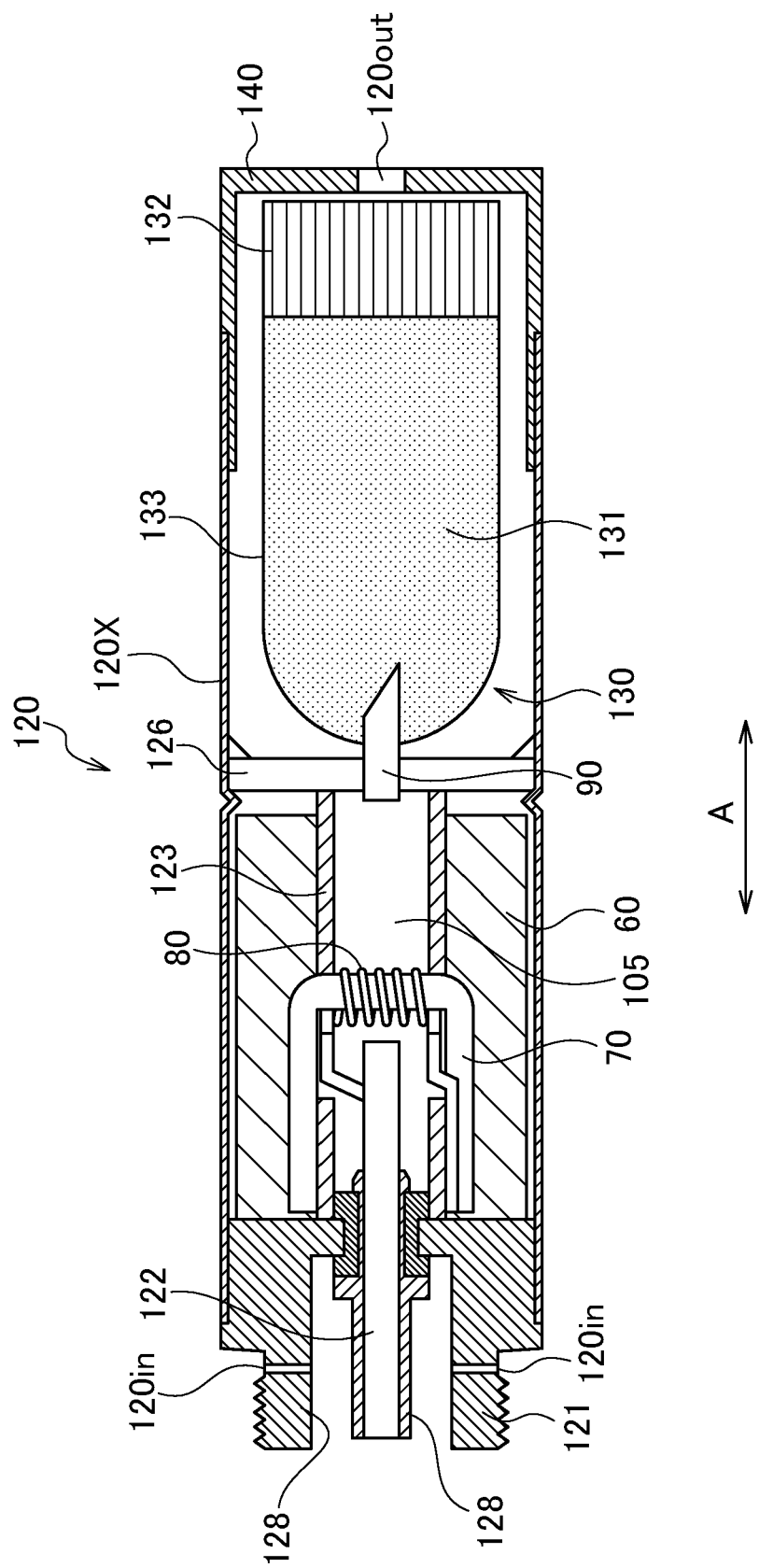
FIG. 3 is a view of an atomization assembly according to the first embodiment.

A non-combustion-type flavor inhaler according to a first embodiment will be described below. FIG. 1 is a view of the non-combustion-type flavor inhaler 100 according to the first embodiment. FIG. 2 is a plan view of a power supply assembly viewed in the direction of an arrow 2A of FIG. 1. FIG. 3 is a view of an atomization assembly according to the first embodiment.

According to the present embodiment, the non-combustion-type flavor inhaler 100 is an equipment for inhalation of a flavor without combustion. The non-combustion-type flavor inhaler 100 has a shape extending in a longitudinal direction A that is the direction from a mouthpiece end E1 toward a non-mouthpiece end E2.

The non-combustion-type flavor inhaler 100 includes the power supply assembly 110 and the atomization assembly 120. The power supply assembly 110 includes a power supply 10 and a control circuit 50. The power supply 10 is, for example, a lithium ion battery. The power supply 10 supplies power necessary for the operation of the non-combustion-type flavor inhaler 100. The power supply 10 supplies the power to, for example, the control circuit 50 and an atomizer 80 included in the atomization assembly 120.

The power supply assembly 110 includes a first case 110X housing at least the power supply 10. The atomization assembly 120 includes a second case 120X housing at least the atomizer 80.

The power supply assembly 110 includes first paired electrodes 118 for electrical connection with the atomizer 80, a first electrode 211, a second electrode 212, and a third electrode 213 electrically connected to the power supply 10.

At least one of the first electrode 211 and the second electrode 212 is electrically connectable to a charger 300 for charging the power supply 10. Note that the first electrode 211, the second electrode 212, and the third electrode 213 are not to be electrically connected to second paired electrodes 128 to be described later, the second paired electrodes 128 being provided to the atomization assembly 120. Specifically, the first electrode 211, the second electrode 212, and the third electrode 213 are preferably disposed at positions at which the first electrode 211, the second electrode 212, and the third electrode 213 cannot be electrically connected to the second paired electrodes 128.

The atomization assembly 120 is detachably attachable to the power supply assembly 110. Specifically, the second case 120X is detachably attachable to the first case 110X. Thus, at least one of the first case 110X and the second case 120X includes engagement for engaging the first case 110X and the second case 120X together. The specific configuration of the engagement is arbitrary. According to the embodiment illustrated in FIG. 1, the engagement includes a female connector 111 and a male connector 121.

More specifically, the power supply assembly 110 has the female connector 111 at a portion adjacent to the atomization assembly 120. The female connector 111 has a spiral groove extending in a direction orthogonal to the longitudinal direction A. The atomization assembly 120 has the male connector 121 at a portion adjacent to the power supply assembly 110. The male connector 121 has a spiral protrusion extending in a direction orthogonal to the longitudinal direction A. Screwing the female connector 111 and the male connector 121 together, allows the atomization assembly 120 and the power supply assembly 110 to be connected mutually. Instead of the embodiment, the atomization assembly 120 may have a female connector and the power supply assembly 110 may have a male connector that screws into the female connector of the atomization assembly.

The first case 110X has a cavity inside. The second case 120X has a cavity inside. When the atomization assembly 120 is attached to the power supply assembly 110, the cavity 104 in the first case 110X is in communication with the cavity 105 in the second case 120X. The second case 120X has a mouthpiece opening 120 out to be used for at least an inhalation action. The mouthpiece opening 120 out is provided at the mouthpiece end E1 of the second case 120X, and is in communication with the cavity 105 in the second case 120X.

The first case 110X and the second case 120X have a ventilation opening 110 in and a ventilation opening 120 in to be used for the inhalation action, respectively. The ventilation opening 110 in is in communication with the cavity 104 in the first case 110X, and the ventilation opening 120 in is in communication with the cavity 105 in the second case 120X. The ventilation opening 110 in and the ventilation opening 120 in are in communication with each other with the female connector 111 and the male connector 121 connected together.

The atomization assembly 120 includes the second paired electrodes 128. The second paired electrodes 128 are provided to the second case 120X. The second paired electrodes 128 are electrically connected with the atomizer 80. When the atomization assembly 120 is attached to the power supply assembly 110, the first paired electrodes 118 and the second paired electrodes 128 are in contact with each other. When the first paired electrodes 118 and the second paired electrodes 128 are in contact with each other, the first paired electrodes 118 and the second paired electrodes 128 are electrically connected together.

With the first paired electrodes 118 and the second paired electrodes 128 electrically connected together, the first paired electrodes 118 are disposed at positions at which conduction of an electric conductor, such as a metallic piece or a metallic plate, is not allowed between the first paired electrodes 118.

Specifically, with the first paired electrodes 118 and the second paired electrodes 128 electrically connected together, at least one of the first paired electrodes 118 is not exposed on the surface of the non-combustion-type flavor inhaler 100. With the first paired electrodes 118 and the second paired electrodes 128 electrically connected together, both of the first paired electrodes 118 are not necessarily exposed on the surface of the non-combustion-type flavor inhaler 100. This arrangement disables an electric conductor, such as a metallic piece or a metallic plate, from conducting between the first paired electrodes 118.

The first electrode 211, the second electrode 212, and the third electrode 213 in the power supply assembly 110, may be provided at any positions of the first case 110X. Preferably, the first electrode 211, the second electrode 212, and the third electrode 213 are provided in an end region of the non-mouthpiece end E2 of the first case 110X.

With the first paired electrodes 118 and the second paired electrodes 128 electrically connected together, the first electrode 211 and the second electrode 212 provided to the power supply assembly 110 are disposed at positions at which an external element, such as a person's finger, different from the constituent elements of the non-combustion-type flavor inhaler, enables the first electrode 211 and the second electrode 212 to be in conduction. Specifically, with the first paired electrodes 118 and the second paired electrodes 128 electrically connected together, the first electrode 211 and the second electrode 212 each have a portion exposed on the surface of the first case 110X.

According to the present embodiment, the exposed portion of the first electrode 211 is positioned on the lateral face of the first case 110X. The exposed portion of the second electrode 212 is positioned on a face facing the longitudinal direction A on the non-mouthpiece end E2 side of the first case 110X. An exposed portion of the third electrode 213 is positioned on a face facing the longitudinal direction A on the non-mouthpiece end E2 side of the first case 110X. An end on the non-mouthpiece end E2 side in the longitudinal direction A of the exposed portion of the third electrode 213, protrudes more than an end on the non-mouthpiece end E2 side in the longitudinal direction A of the exposed portion of the second electrode 212. That is, the exposed portion of the second electrode 212 and the exposed portion of the third electrode 213 are provided on the faces facing the same direction in the first case 110X, and there is a difference in level between the end face of the exposed portion of the second electrode 212 and the end face of the exposed portion of the third electrode 213. An insulating member 215 insulating the first electrode 211, the second electrode 212, and the third electrode 213, is provided. The lateral face of the first case 210X is provided with an opening 214 in communication with aerial space. The opening 214 may be provided between the first electrode 211 and a sensor 20 to be described later. According to the present embodiment, the opening 214 is provided on the lateral face of the first case 110X instead of on the end face on the non-mouthpiece end E2 side.

In the example illustrated in FIG. 1, the end on the non-mouthpiece end E2 side in the longitudinal direction A of the exposed portion of the third electrode 213, protrudes more than the end on the non-mouthpiece end E2 side in the longitudinal direction A of the exposed portion of the second electrode 212. Instead of this, the end on the non-mouthpiece end E2 side in the longitudinal direction A of the exposed portion of the second electrode 212, may protrude more than the end on the non-mouthpiece end E2 side in the longitudinal direction A of the exposed portion of the third electrode 213.

As illustrated in FIG. 1, the exposed portion of the first electrode 211 and the exposed portion of the second electrode 212 are preferably disposed on the faces facing mutually the different directions in the first case 110X. This arrangement can inhibit an electric conductor, such as a metallic piece or a metallic plate, from conducting unexpectedly between the respective exposed portions of the first electrode 211 and the second electrode 212.

The positions of the first electrode 211, the second electrode 212, and the third electrode 213 may be replaced with each other. For example, the third electrode 213 may be disposed at the position of the first electrode 211 illustrated in FIG. 1 and the first electrode 211 may be disposed at the position of the third electrode 213 illustrated in FIG. 1. In this case, the exposed portion of the first electrode 211 and the exposed portion of the second electrode 212 are provided on the faces facing the same direction in the first case 110X, and there is a difference in level between the end face of the exposed portion of the first electrode 211 and the end face of the exposed portion of the second electrode 212. Even in this case, the presence of the difference in level between the position of the first electrode 211 and the position of the second electrode 212, can inhibit an electric conductor, such as a metallic piece or a metallic plate, from conducting unexpectedly between the respective exposed portions of the first electrode 211 and the second electrode 212. From this viewpoint, the difference in level between the first electrode 211 and the second electrode 212 is preferably 0.5 mm or more.

Furthermore, the difference in level between the first electrode 211 and the second electrode 212, is so sufficient that a finger of a user can make conduction easily between the first electrode 211 and the second electrode 212. Specifically, the difference in level is preferably 5 mm or less, more preferably 3 mm or less, and even more preferably 1 mm or less. Note that the difference in level may be formed such that the first electrode 211 protrudes more than the second electrode 212 or may be formed such that the second electrode 212 protrudes more than the first electrode 211.

The power supply assembly 110 may further include the sensor 20 and a light-emitting element 40. The sensor 20 detects the inhalation action of the user. In detail, the sensor 20 detects the difference in internal pressure between a cavity closer to the non-mouthpiece end E2 side than the sensor 20 and a cavity closer to the mouthpiece end E1 side than the sensor 20 is.

Figure 4:
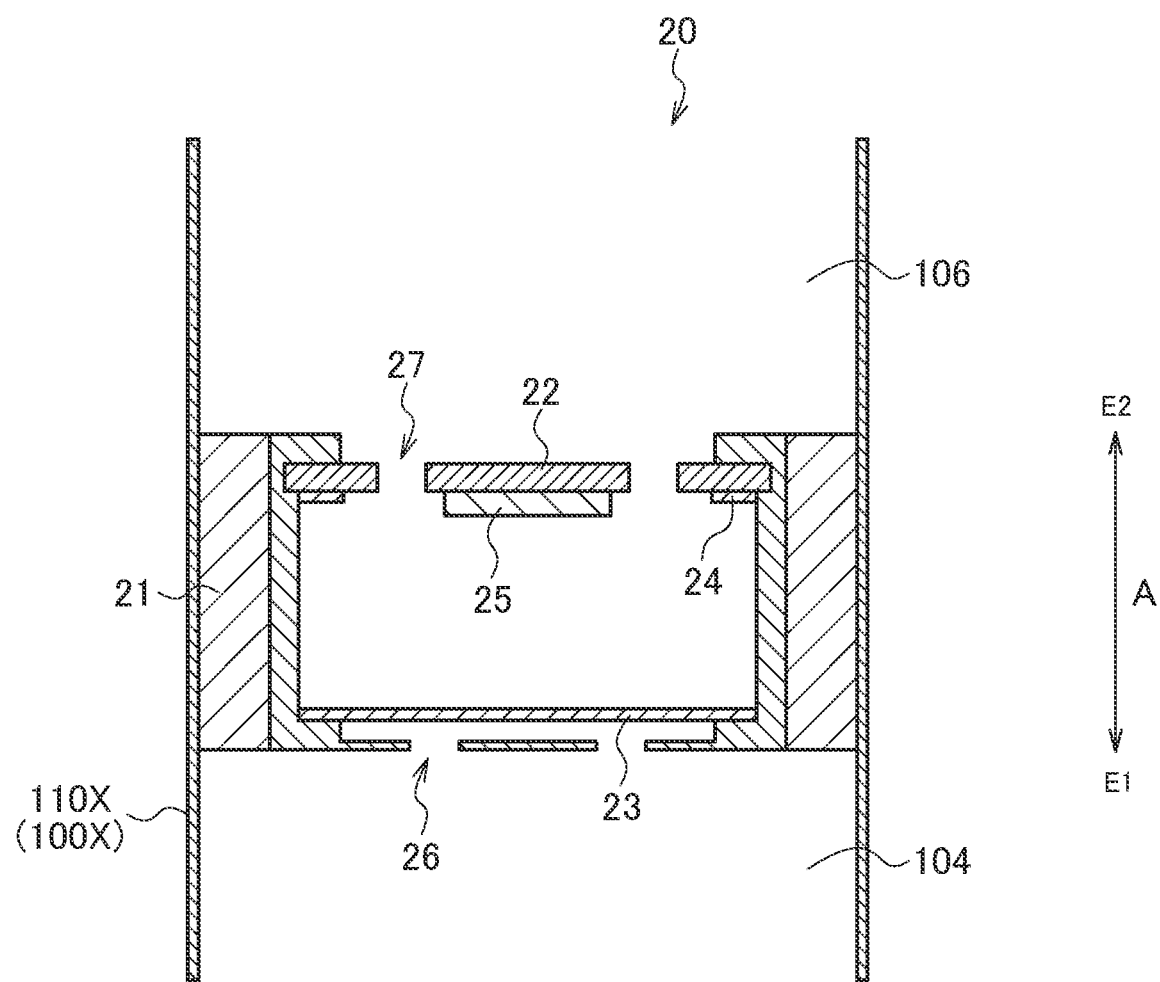
FIG. 4 is a view of a sensor according to the first embodiment.

FIG. 4 illustrates an exemplary specific structure of the sensor 20. The first case 110X includes: the first cavity 104 provided on the mouthpiece end E1 side with respect to the sensor 20; and a second cavity 106 provided on the non-mouthpiece end E2 side with respect to the sensor 20. The sensor 20 detects the difference in internal pressure between the first cavity 104 and the second cavity 106.

For example, the sensor 20 includes a capacitor, and outputs a value (e.g., a voltage value) indicating the electrical capacitance of the capacitor corresponding to the difference in internal pressure between the first cavity 104 and the second cavity 106. The sensor 20 includes a cover 21, a substrate 22, an electrode film 23, a fixed electrode 24, a control circuit 25, an opening 26, and an opening 27, as illustrated in FIG. 4. There is no gap between the cover 21 and the first case 110X, and the first cavity 104 and the second cavity 106 are segmented by the sensor 20 such that the first cavity 104 and the second cavity 106 are out of communication with each other in the first case 110X. The substrate 22 is provided with the fixed electrode 24 and the control circuit 25. The electrode film 23 deforms in response to a variation in the difference in internal pressure between the first cavity 105 and the second cavity 106. The fixed electrode 24 forms the electrode film 23 and the capacitor. The electrical capacitance of the capacitor varies due to the deformation of the electrode film 23. The control circuit 25 detects the electrical capacitance varying due to the deformation of the electrode film 23. The opening 26 is in communication with the first cavity 104. Therefore, the inhalation action changes the internal pressure of the first cavity 104, so that the electrode film 23 deforms. The opening 27 is in communication with the second cavity 106. Therefore, a predetermined action changes the internal pressure of the second cavity 106, so that the electrode film 23 deforms.

Specifically, for example, in a case where the inhalation action is performed, the internal pressure of the first cavity 104 decreases, whereas the internal pressure of the second cavity 106 does not substantially vary and is substantially equal to atmospheric pressure. Thus, the sensor 20 detects substantially the variation in the pressure of the first cavity 104. For example, in a case where a blow action is performed, the internal pressure of the first cavity 104 increases, whereas the internal pressure of the second cavity 106 does not substantially vary and is substantially equal to atmospheric pressure. Thus, the sensor 20 detects substantially the variation in the pressure of the first cavity 104. For example, in a case where the predetermined action is performed, the internal pressure of the second cavity 106 increases, whereas the internal pressure of the first cavity 104 does not substantially vary and is substantially equal to atmospheric pressure. Thus, the sensor 20 detects the variation in the pressure of the second cavity 106.

The light-emitting element 40 is a light source, such as an LED or an electric light. The light-emitting element 40 provides notification of the state of the non-combustion-type flavor inhaler 100, in a light-emitting mode, namely, light-emitting color, lighting/non-lighting, or a light-intensity pattern during lighting. The state of the non-combustion-type flavor inhaler 100 may be a state such as power-on or power-off, or a state such as an inhalation state or a non-inhalation state.

The control circuit 50 controls the operation of the non-combustion-type flavor inhaler 100. Note that the details of the control circuit 50 will be described later.

The atomization assembly 120 includes a reservoir 60, a liquid retaining member 70, the atomizer 80, a destroyer 90, a capsule unit 130, and a mouthpiece unit 140. Here, the atomization assembly 120 includes: the opening 120 in for taking in the atmosphere inside; an air conduit 122 that communicates with the power supply assembly 110 through the male connector 121; and a ceramic 123 disposed in a tubular shape. The second case 120X has a cylindrical shape forming the outer form of the atomization assembly 120. A space surrounded by the ceramic 123 forms an air conduit. That is the space surrounded by the ceramic 123 and the air conduit 122 described above form part of the cavity 105.

The reservoir 60 stores an aerosol source. The reservoir 60 is a porous body made of a material such as a resin web. The reservoir 60 is required at least to be disposed at a position at which the aerosol source can be supplied to the liquid retaining member 70, the reservoir 60 being at least in contact with part of the liquid retaining member 70.

Note that, according to the embodiment, because the ceramic 123 described above is disposed inside the reservoir 60, the aerosol source retained by the reservoir 60 is inhibited from volatilizing.

The liquid retaining member 70 retains the aerosol source supplied from the reservoir 60. For example, the liquid retaining member 70 is a wick made of glass fiber.

The atomizer 80 atomizes the aerosol source retained by the liquid retaining member 70, without combustion. For example, the atomizer 80 is a resistance heating element that heats due to the power supplied to the atomizer 80. The atomizer 80 may include a wire wound around the liquid retaining member 70.

According to the embodiment, a heating type of component that atomizes the aerosol source with heating, has been exemplified as the atomizer 80. However, the atomizer is required at least to have a function of atomizing the aerosol source, and thus may be an ultrasonic type of component that atomizes the aerosol source with ultrasonic waves.

The destroyer 90 is a member for destroying part of a predetermined film 133 with the capsule unit 130 attached. According to the embodiment, the destroyer 90 is retained by a partition wall member 126 for a partition between the atomization assembly 120 and the capsule unit 130. The partition wall member 126 is, for example, a polyacetal resin. The destroyer 90 is, for example, a cylindrical hollow needle extending in the longitudinal direction A. Puncturing the predetermined film 133 with the tip of the hollow needle, destroys the part of the predetermined film 133. A space inside the hollow needle forms an air conduit interconnecting the atomization assembly 120 and the capsule unit 130 so that air passes through the air conduit. Here, a mesh having a degree of fineness through which raw material included in a tobacco source 131 does not pass, is preferably provided inside the hollow needle.

The embodiment is not limited to this, and thus the destroyer 90 may be a portion adjacent to the predetermined film 133 with the capsule unit 130 attached. The user may pressurize this type of portion to destroy part of the predetermined film 133.

The capsule unit 130 is detachably attachable to a main body unit. The capsule unit 130 includes the tobacco source 131, a filter 132, and the predetermined film 133. The tobacco source 131 is filled in a space segmented by the predetermined film 133 and the filter 132. Here, the main body unit includes a portion excluding the capsule unit 130 from the atomization assembly 120. For example, the main body unit includes the reservoir 60 described above, the liquid retaining member 70, and the atomizer 80.

The tobacco source 131 is provided such that the tobacco source 131 is closer to the mouthpiece end E1 side than the reservoir 60 retaining the aerosol source is. The tobacco source 131 generates the flavor to be inhaled by the user together with aerosol generated from the aerosol source. Examples of the tobacco source 131 that can be used, include shredded tobacco, a compact including tobacco raw material formed in a granular shape, and a compact including the tobacco raw material formed in a sheet shape. An aroma, such as menthol, may be added to the tobacco source 131.

The filter 132 is adjacent to the mouthpiece end E1 side with respect to the tobacco source 131, and includes a substance having breathability. For example, the filter 132 is preferably an acetate filter. The filter 132 preferably has a degree of fineness through which the raw material included in the tobacco source 131 does not pass.

The predetermined film 133 is integrally formed with the filter 132, and includes a member having no breathability. The predetermined film 133 covers a portion excluding a portion adjacent to the filter 132, from the outer surface of the tobacco source 131.

The mouthpiece unit 140 has the mouthpiece opening 120 out. The mouthpiece opening 120 out exposes the filter 132. The user inhales the aerosol from the mouthpiece opening 120 out to inhale the flavor together with the aerosol. According to the embodiment, the mouthpiece unit 140 is detachably attachable to the capsule unit 130. Instead of this, the mouthpiece unit 140 may be provided integrally with the capsule unit 130. In this case, it should be noted that the mouthpiece unit 140 is included in part of the capsule unit 130.

(Charger)

Figure 5:
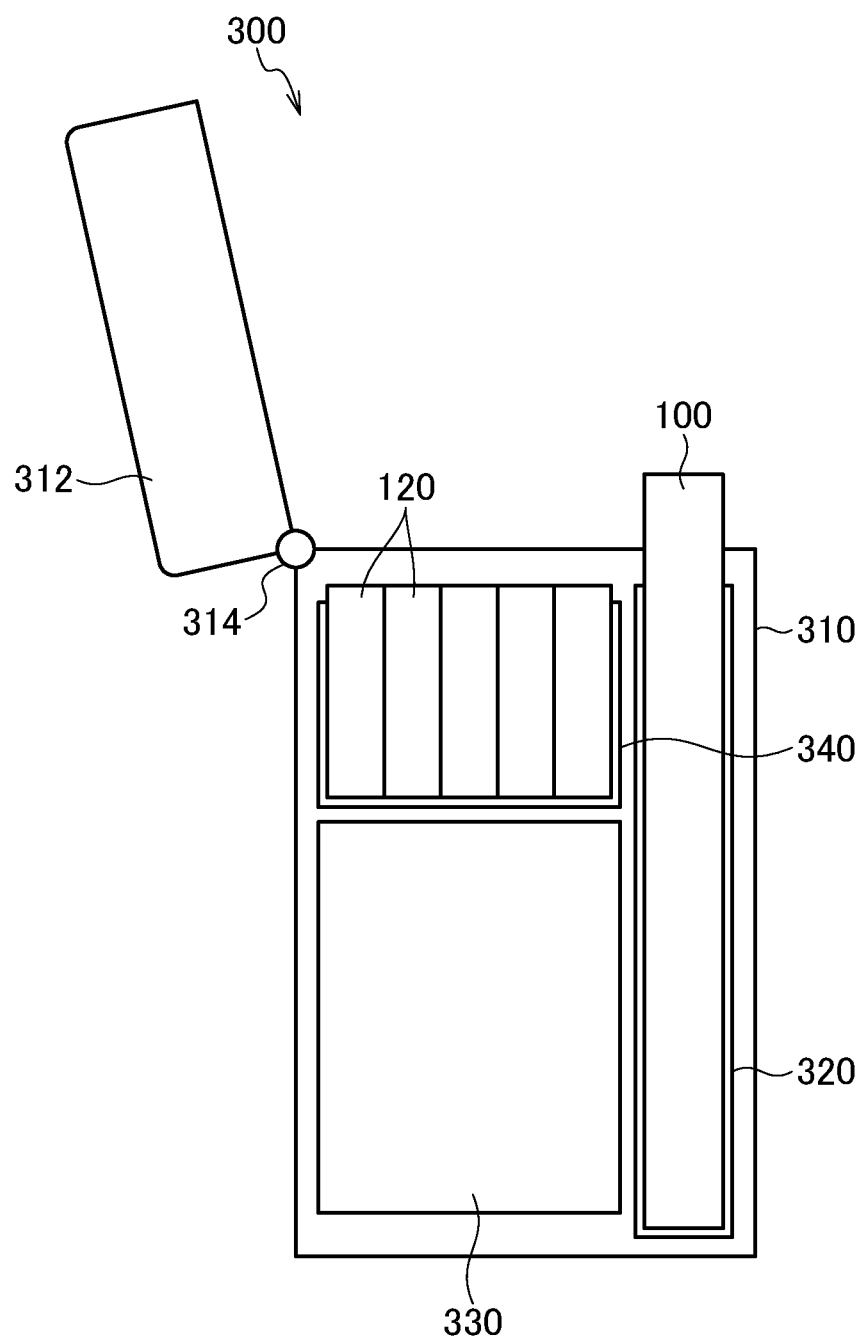
FIG. 5 is a view of a charger that charges a power supply of the non-combustion-type flavor inhaler.

FIG. 5 illustrates the charger 300 that charges the power supply 10 of the non-combustion-type flavor inhaler 100. The charger 300 is detachably attachable to the non-combustion-type flavor inhaler 100, and is capable of supplying a charging current to the non-combustion-type flavor inhaler 100. The non-combustion-type flavor inhaler 100 and the charger 300 are included in a non-combustion-type flavor inhalation system. The charger 300 is a device for charging the power supply 10 provided to the non-combustion-type flavor inhaler 100.

The charger 300 may include a case 310 and a lid 312 openable and closable with a hinge 314. The charger 300 includes a secondary battery 330, and the secondary battery 330 is electrically connectable to an external power supply through a power cable. The power cable may be a cable for connection to an AC power supply as the external power supply. Instead of this, the power cable may be a universal serial bus (USB) cable for connection to an electronic device as the external power supply.

The charger 300 includes a holder 320 capable of retaining the non-combustion-type flavor inhaler 100. The case 310 may include a housing 340 that houses a plurality of exchangeable atomization assemblies 120.

The holder 320 retains the non-combustion-type flavor inhaler 100 such that the non-combustion-type flavor inhaler 100 stands. The holder 320 is provided with paired electrodes 332 for charging the power supply 10 provided to the power supply assembly 110 of the non-combustion-type flavor inhaler 100. The paired electrodes 332 of the charger 300 are electrically connected with the secondary battery 330. According to the present embodiment, with the non-combustion-type flavor inhaler 100 retained by the holder 320, the second electrode 212 and the third electrode 213 of the power supply assembly 110 are electrically connected with the paired electrodes 332 of the charger 300 (also refer to FIG. 7).

(Control Circuit)

Figure 6:
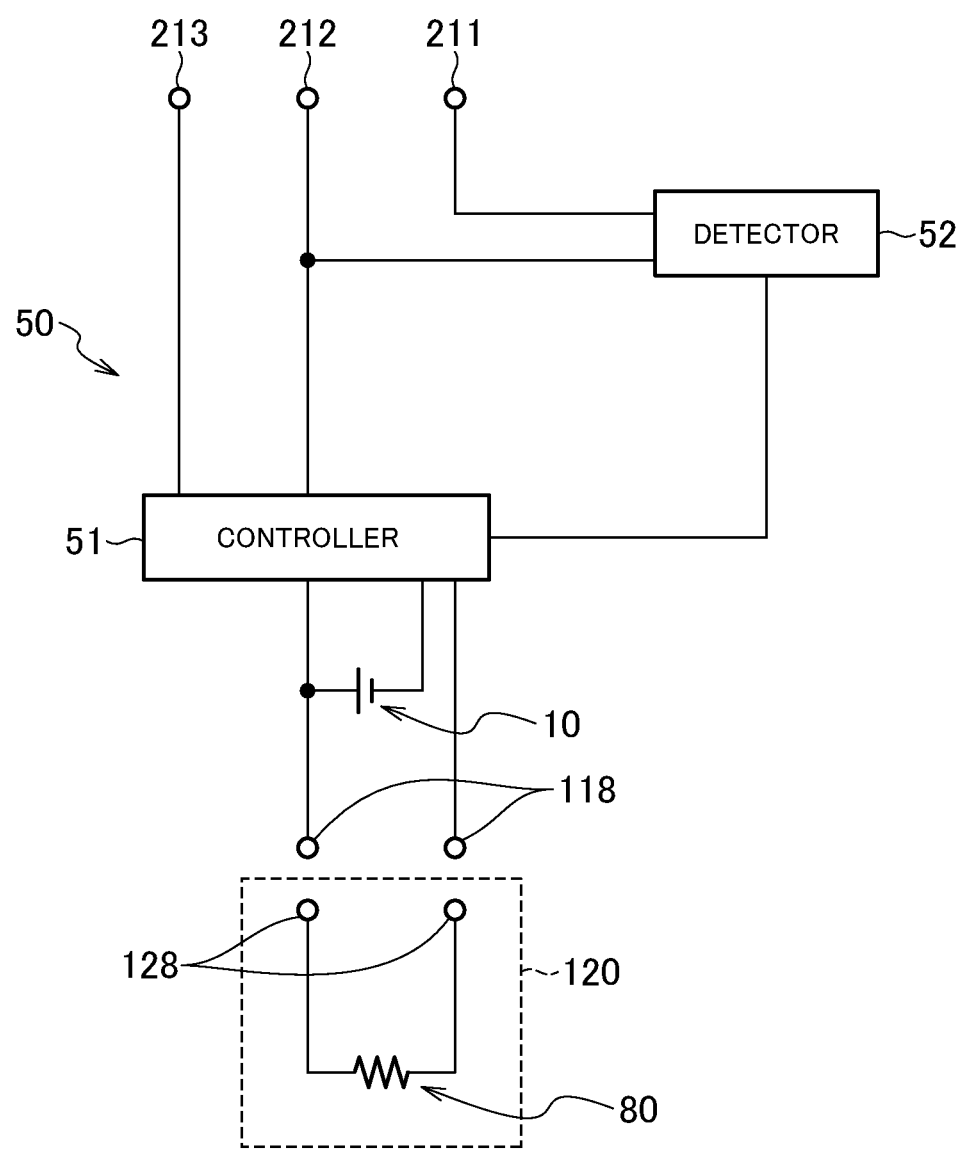
FIG. 6 is a schematic diagram of a control circuit according to the first embodiment.

The control circuit 50 according to the embodiment will be described below. FIG. 6 illustrates the control circuit 50 according to the present embodiment. FIG. 6 illustrates the circuit with the atomization assembly 120 removed from the power supply assembly 110. With the atomization assembly 120 attached to the power supply assembly 110, the first paired electrodes 118 are electrically connected with the second paired electrodes 128.

The control circuit 50 includes a controller 51 for at least controlling the power from the power supply 10 to the atomizer 80. The controller 51 performs atomization control of the atomizer 80 to start or finish the atomization of the aerosol source, on the basis of at least the inhalation action. The controller 51 may control the atomizer 80, on the basis of an output value of the sensor 20 that detects the inhalation action.

Figure 7:
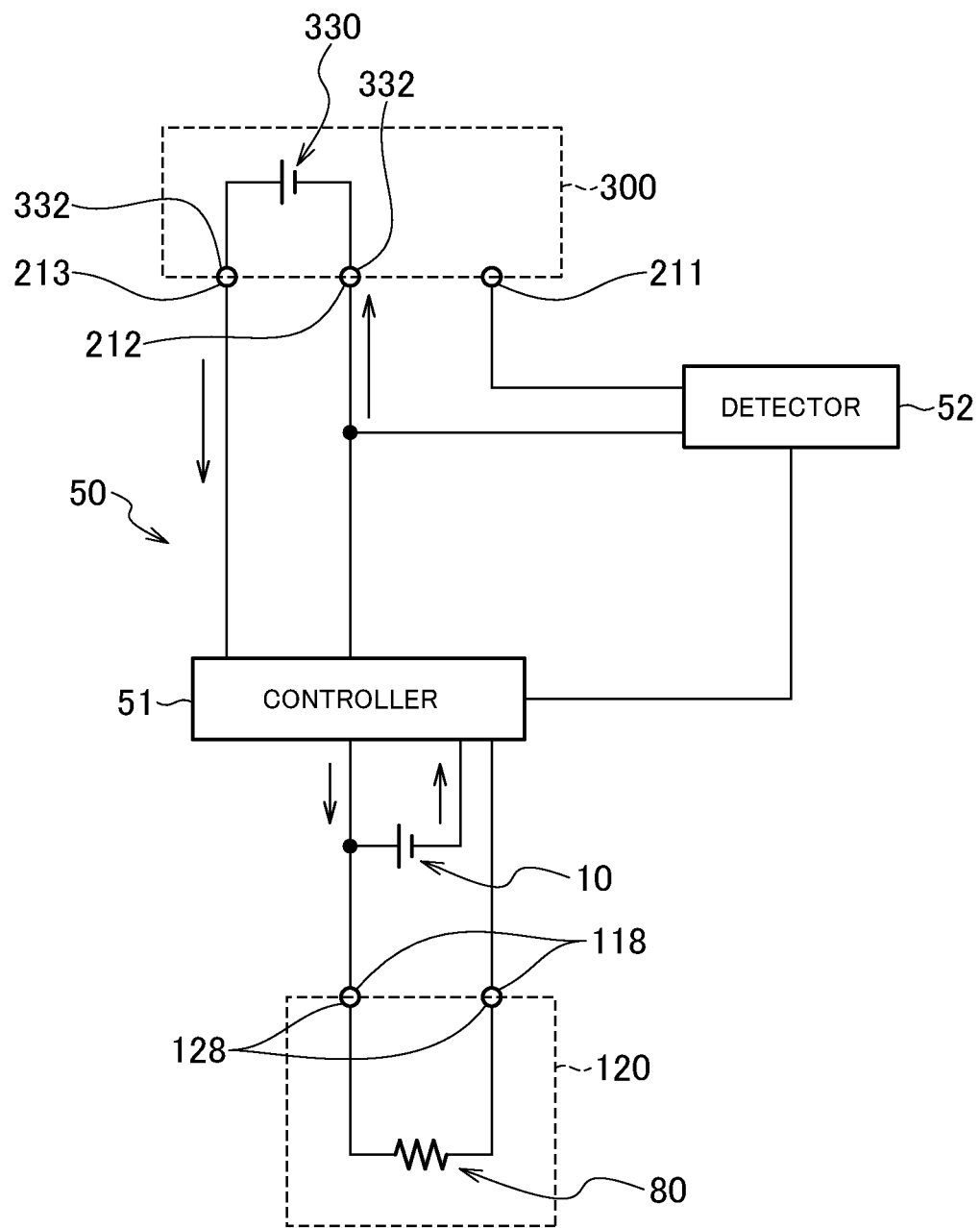
FIG. 7 is a schematic diagram of the flow of a current during charging in the control circuit according to the first embodiment.

FIG. 7 illustrates the flow of a current during charging in the control circuit 50. According to the present embodiment, when the non-combustion-type flavor inhaler 100 is inserted into the holder 320 of the charger 300, the second electrode 212 and the third electrode 213 of the power supply assembly 110 are electrically connected with the paired electrodes 332 on the charger 300 side. The charger 300 supplies the charging current to the power supply 10 of the power supply assembly 110 through the second electrode 212 and the third electrode 213. This arrangement can charge the power supply 10. Note that FIG. 7 illustrates, with an arrow, the direction of the flow of the current during charging.

The first electrode 211 of the power supply assembly 110 does not contribute to supply of the charging current supplied from the charger 300 to the power supply 10. The first electrode 211 that does not contribute to the supply of the charging current, may be provided at a position at which the first electrode 211 is physically out of contact with the charger 300. Instead of this, the first electrode 211 that does not contribute to the supply of the charging current, may be physically in contact with the charger 300 through an insulator inhibiting electrical connection with the charger 300. The first electrode 211 that does not contribute to the supply of the charging current, may be electrically connected with the charger 300. In this case, the first electrode 211 is electrically connected with an electrode provided to the charger 300, the electrode no contributing to the supply of the charging current from the charger 300 to the power supply 10.

Figure 8:
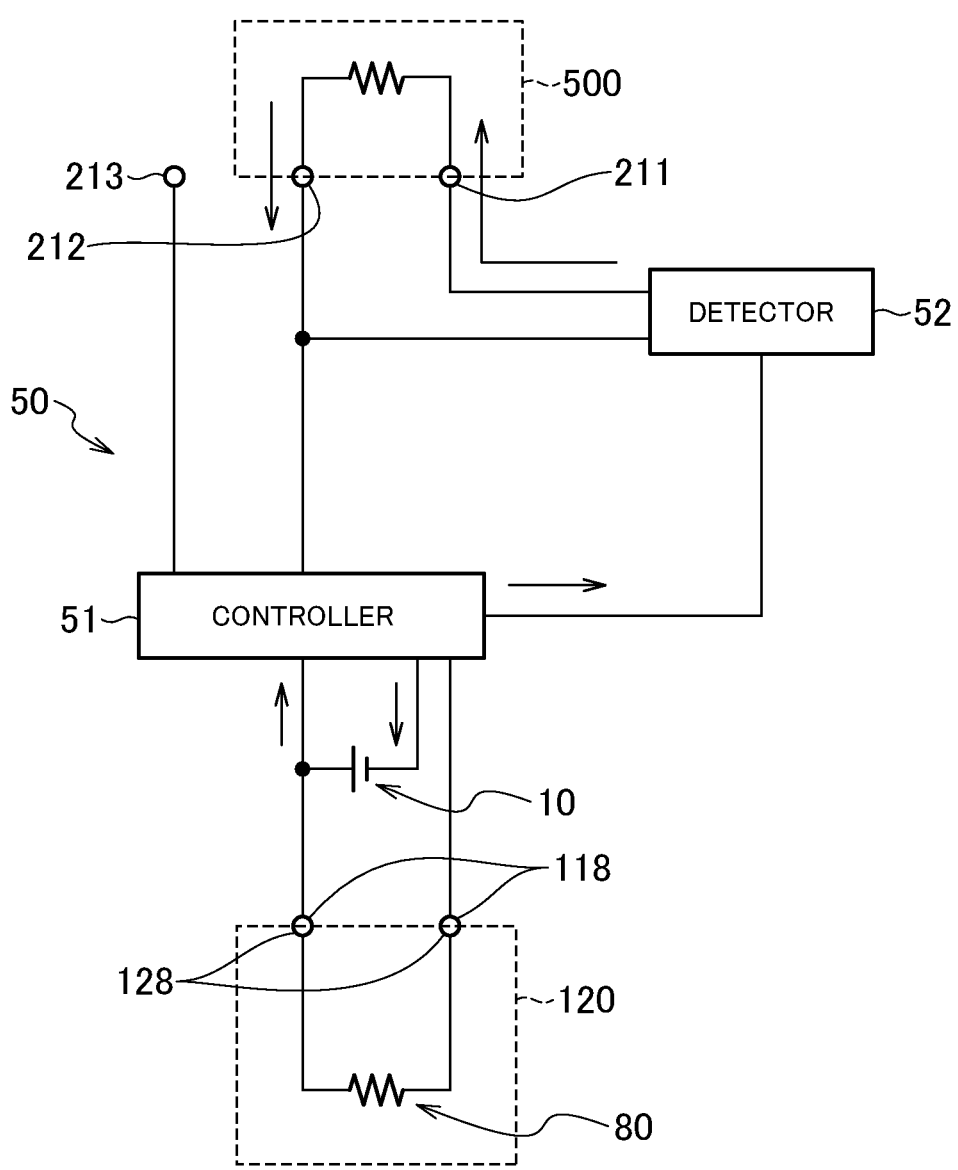
FIG. 8 is a schematic diagram of the flow of a current when a first electrode and a second electrode are in conduction in the control circuit according to the first embodiment.

FIG. 8 is a schematic diagram of the flow of a current when the first electrode 211 and the second electrode 212 are in conduction in the control circuit 50 according to the first embodiment. For example, when an external element 500, such as a finger of the user, touches the first electrode 211 and the second electrode 212 simultaneously, the first electrode 211 and the second electrode 212 are mutually in conduction as illustrated in FIG. 8. At this time, the power from the power supply 10 allows a predetermined current to flow between the first electrode 211 and the second electrode 212. The predetermined current flows in the opposite direction to that of the charging current, at least at the second electrode 212. Note that FIG. 8 illustrates, with an arrow, the direction of the predetermined current when the first electrode 211 and the second electrode 212 are in conduction.

The control circuit 50 includes a detector 52 that detects the predetermined current in the opposite direction to the direction of the current (charging current) flowing through the second electrode 212 when the charger 300 charges the power supply 10. The detector 52 may be disposed at a position into which no charging current flows but the predetermined current in the opposite direction to the direction of the charging current flows. As a specific example, the detector 52 is disposed at a position at which the detector 52 couples the first electrode 211 and the second electrode 212 together. This arrangement enables the detector 52 to detect the presence or absence of the predetermined current that flows between the first electrode 211 and the second electrode 212. This arrangement enables the control circuit 50 to determine whether the first electrode 211 and the second electrode 212 are mutually in conduction due to the external element. Therefore, the control circuit 50 can detect whether the user has touched the first electrode 211 and the second electrode 212 simultaneously.

According to the present embodiment, when the detector 52 detects the present or absence of the predetermined current that flows between the first electrode 211 and the second electrode 212, the control circuit 50 detects the conduction between the first electrode 211 and the second electrode 212. However, the detection of the conduction between the first electrode 211 and the second electrode 212, is not limited to this mode. For example, the control circuit 50 may be capable of detecting the difference between the direction of the current during charging and the direction of the current when the first electrode 211 and the second electrode 212 are in conduction. Even in this case, the control circuit 50 can detect whether the first electrode 211 and the second electrode 212 are mutually in conduction due to the external element.

The non-combustion-type flavor inhaler 100 may include display means for notifying the user that the detector 52 has detected the predetermined current. The display means may be, for example, the light-emitting element 40 described above. The light-emitting mode of the light-emitting element 40 can notify the user of the detection of the predetermined current.

The control circuit 50 performs predetermined control, on the basis of a detected result of the predetermined current in the opposite direction to the direction of the current flowing through the second electrode 212 when the charger 300 charges the power supply 10. For example, the control circuit 50 performs the predetermined control in response to the length of a period of the detection of the predetermined current. As an example, when the control circuit 50 has detected the predetermined current for several seconds, the control circuit 50 performs the predetermined control. Note that, when the control circuit 50 has continuously detected the predetermined current for a predetermined time (first threshold value) or more, the control circuit 50 favorably cancels the predetermined control. For example, when the control circuit 50 has continuously detected the predetermined current for a time of the first threshold value or more while the light-emitting element 40 is reporting information as the predetermined control, the control circuit 50 cancels the report of the information of the light-emitting element 40. When the control circuit 50 has continuously detected the predetermined current for a time of the first threshold value or more during performance of user authentication or switching control between modes to be used, as the predetermined control, the control is canceled.

Alternatively, the control circuit 50 may perform the predetermined control when the control circuit 50 has detected the predetermined current a plurality of times within a predetermined period (second threshold value). For example, when the control circuit 50 has detected the predetermined current three times for several seconds, the control circuit 50 performs the predetermined control.

When the control circuit 50 detects the predetermined current generated by the external element 500 different from the constituent elements of the non-combustion-type flavor inhaler 100, the control circuit 50 may perform the predetermined control, on the basis of the level of an electric resistance value of the external element 500. The detection of the electric resistance value of the external element 500 enables the control circuit 50 to distinguish whether the external element 500 is a person's finger or a different object. For example, in a case where the electric resistance value of the external element is less than 100Ω, preferably less than 10Ω, the control circuit 50 may determine that the external element 500 is not the person's finger, not to perform the predetermined control. The control circuit 50 may be capable of directly detecting the electric resistance value of the external element that brings the first electrode 211 and the second electrode 212 into conduction. Instead of this, the control circuit 50 may be capable of detecting a current value and a voltage value to estimate the electric resistance value of the external element from the detected current value and the detected voltage value. The detection or estimation of the electric resistance value of the external element by the control circuit 50, enables the predetermined control not to be performed for an operation by a different external element having a lower electric resistance value than that of the person's finger.

Furthermore, the control circuit 50 detects whether the power supply 10 is being charged, and the control circuit 50 preferably does not perform, when detecting the charging of the power supply 10, the predetermined control regardless of the detected result of the predetermined current.

The predetermined control may include determining whether the user is an authorized user. Alternatively, in a case where a plurality of operation modes is provided as the operation mode of the non-combustion-type flavor inhaler 100, the predetermined control may include switching between the operation modes. The switching between the operation modes is, for example, switching between a sleep mode in which the atomization control of atomizing the aerosol source is not allowed (power-saving mode) and a ready mode in which the aerosol source is allowed to be atomized. Alternatively, the switching between the operation modes is switching of the intensity of power supply output to the atomizer 80 (the absolute value or duty cycle of the power supply output). Alternatively, in a case where the non-combustion-type flavor inhaler 100 includes a communication module, the switching between the operation modes is switching of whether communication with the communication module is allowed. Alternatively, the predetermined control may be reset control of a value counted by the controller 51 (e.g., the accumulated number of puff actions, the accumulated number of puff actions in an one-time puff-action series, or the accumulated number of puff-action series). Note that the puff-action series means a series of actions in which the inhalation action is repeated predetermined times. Alternatively, the predetermined control may include providing, in the light-emitting mode of the light-emitting element 40, notification of a value managed by the controller 51 (e.g., the accumulated number of puff actions, the accumulated number of puff actions in an one-time puff-action series, the accumulated number of puff-action series, the remaining quantity of the power supply 10, the remaining quantity of the aerosol source, or whether the communication with the communication module is ready to perform).

According to the first embodiment, the charger 300 supplies the charging current to the power supply 10 through the second electrode 212 and the third electrode 213. Instead of this, the charger 300 may supply the charging current to the power supply 10 through the first electrode 211 and the third electrode 213. In this case, the second electrode 212 is an electrode that does not contribute to supply of the charging current supplied from the charger 300 to the power supply 10. In this manner, the charging current from the charger 300 to the power supply 10 is required at least to be supplied to the power supply assembly 110 through the third electrode 213 and only one of the first electrode 211 and the second electrode 212.

Second Embodiment

A non-combustion-type flavor inhaler 100A according to a second embodiment will be described below. Note that the same constituents as those of the non-combustion-type flavor inhaler according to the first embodiment, are denoted with the same reference signs, and thus the descriptions thereof will be omitted. Differences from the first embodiment will be mainly described below.

Figure 9:
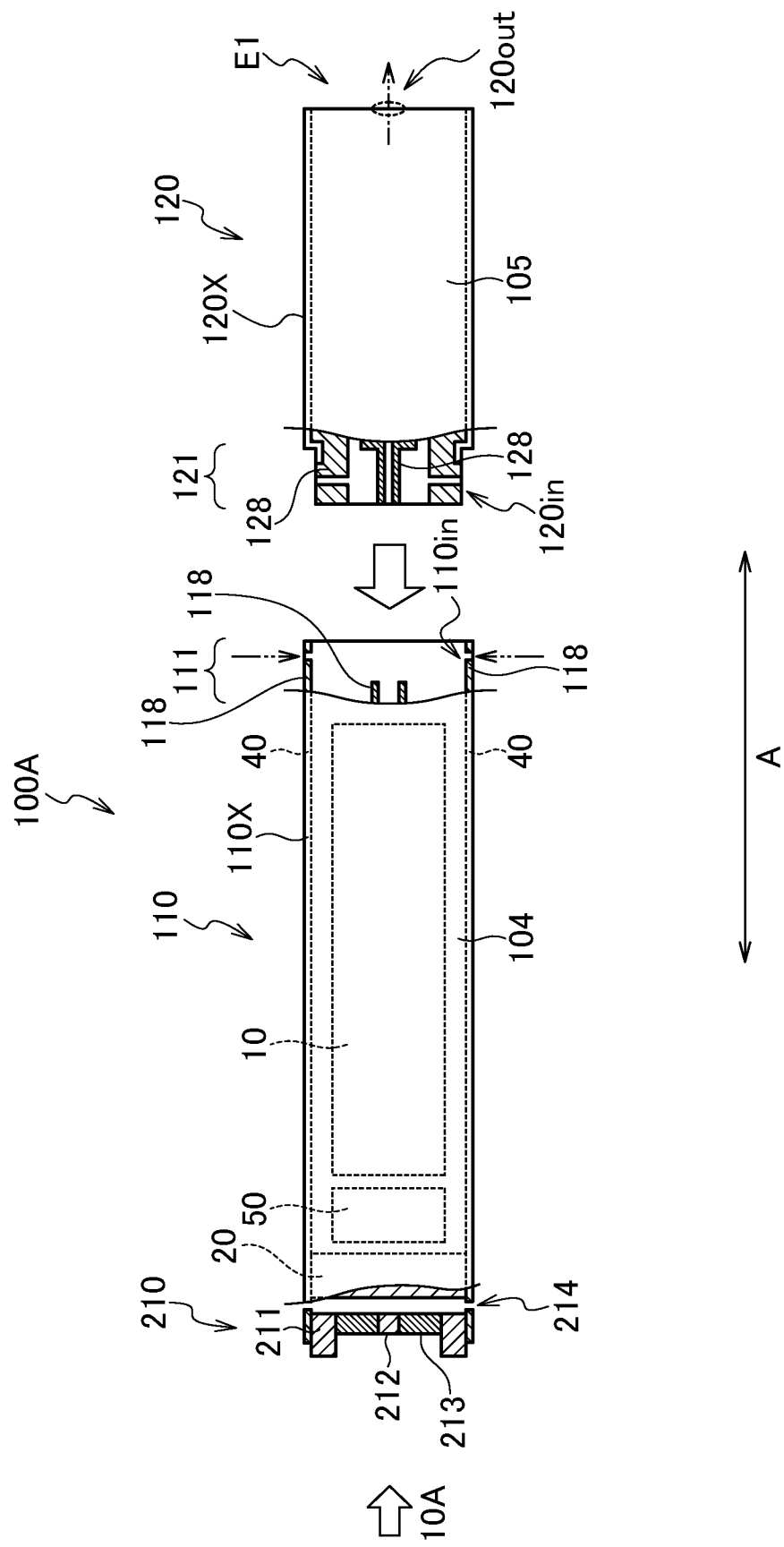
FIG. 9 is a view of a non-combustion-type flavor inhaler according to a second embodiment.
Figure 10:
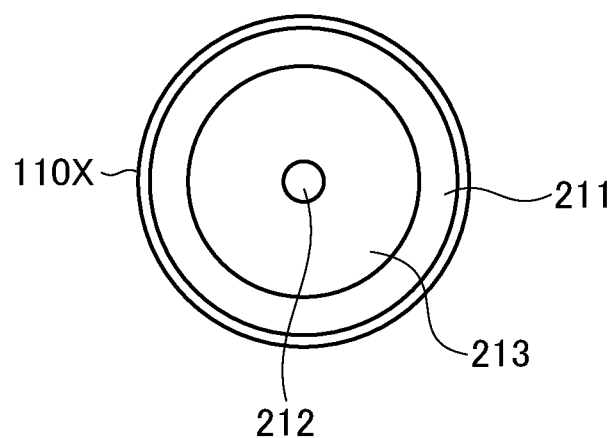
FIG. 10 is a plan view of a power supply assembly viewed in the direction of an arrow 10 of FIG. 9.

FIG. 9 is a view of the non-combustion-type flavor inhaler 100A according to the second embodiment. FIG. 10 is a plan view of a power supply assembly viewed in the direction of an arrow 10A of FIG. 9. According to the second embodiment, the power supply assembly 110 includes a first electrode 211 and a second electrode 212. It should be noted that the first electrode 211 and the second electrode 212 are not to be connected with paired electrodes 128 of an atomization assembly 120. According to the second embodiment, the third electrode 213 indicated in the first embodiment is not provided. According to the second embodiment, both of the first electrode 211 and the second electrode 212 are to be electrically connected with paired electrodes 332 of a charger 300.

The first electrode 211 and the second electrode 212 may be provided at any positions of a first case 110X. The first electrode 211 and the second electrode 212 are preferably provided in an end region of a non-mouthpiece end E2 of the first case 110X.

According to the second embodiment, an exposed portion of the first electrode 211 is positioned on a face facing a longitudinal direction A on the non-mouthpiece end E2 side of the first case 110X. An exposed portion of the second electrode 212 is positioned on a face facing the longitudinal direction A on the non-mouthpiece end E2 side of the first case 110X. The end face on the non-mouthpiece end E2 side in the longitudinal direction A of the exposed portion of the first electrode 211, protrudes more than the end face on the non-mouthpiece end E2 side in the longitudinal direction A of the exposed portion of the second electrode 212. That is the exposed portion of the first electrode 211 and the exposed portion of the second electrode 212 are provided on the faces facing the same direction in the first case 110X, and there is a difference in level between the end face of the exposed portion of the first electrode 211 and the end face of the exposed portion of the second electrode 212. This arrangement can inhibit an electric conductor, such as a metallic piece or a metallic plate, from conducting unexpectedly between the respective exposed portions of the first electrode 211 and the second electrode 212. From this viewpoint, the difference in level between the first electrode 211 and the second electrode 212 is preferably 0.5 mm or more.

Furthermore, the difference in level between the first electrode 211 and the second electrode 212, is so sufficient that a finger of a user can make conduction easily between the first electrode 211 and the second electrode 212. Specifically, the difference in level is preferably 5 mm or less, more preferably 3 mm or less, and even more preferably 1 mm or less. Note that, instead of the example illustrated in FIG. 9, the difference in level may be formed such that the end face on the non-mouthpiece end E2 side in the longitudinal direction A of the exposed portion of the second electrode 212, protrudes more than the end face on the non-mouthpiece end E2 side in the longitudinal direction A of the exposed portion of the first electrode 211.

Figure 11:
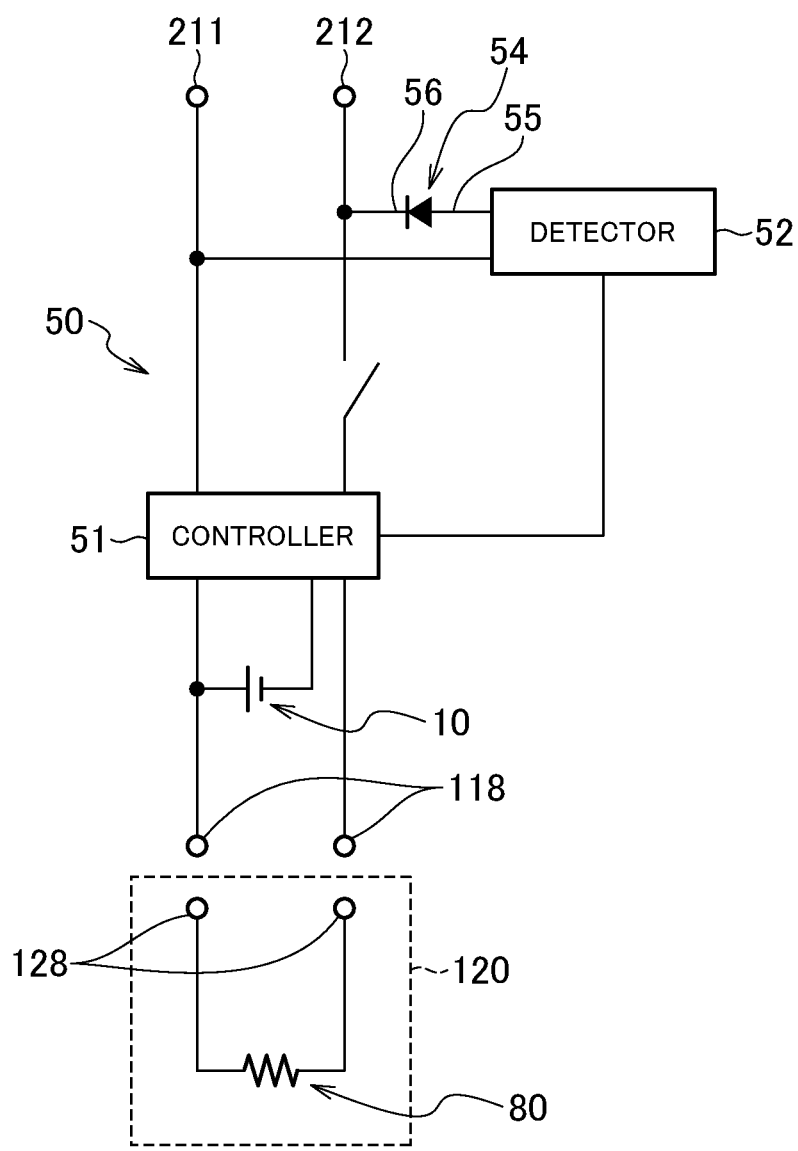
FIG. 11 is a schematic diagram of a control circuit according to the second embodiment.

Next, the details of a control circuit 50 according to the second embodiment will be described. FIG. 11 is a schematic diagram of the control circuit according to the second embodiment. The control circuit 50 includes a controller 51 for at least controlling power from a power supply 10 to an atomizer 80. A detector 52 is provided between an electric wire extending from the first electrode 211 and an electric wire extending from the second electrode 212.

Figure 12:
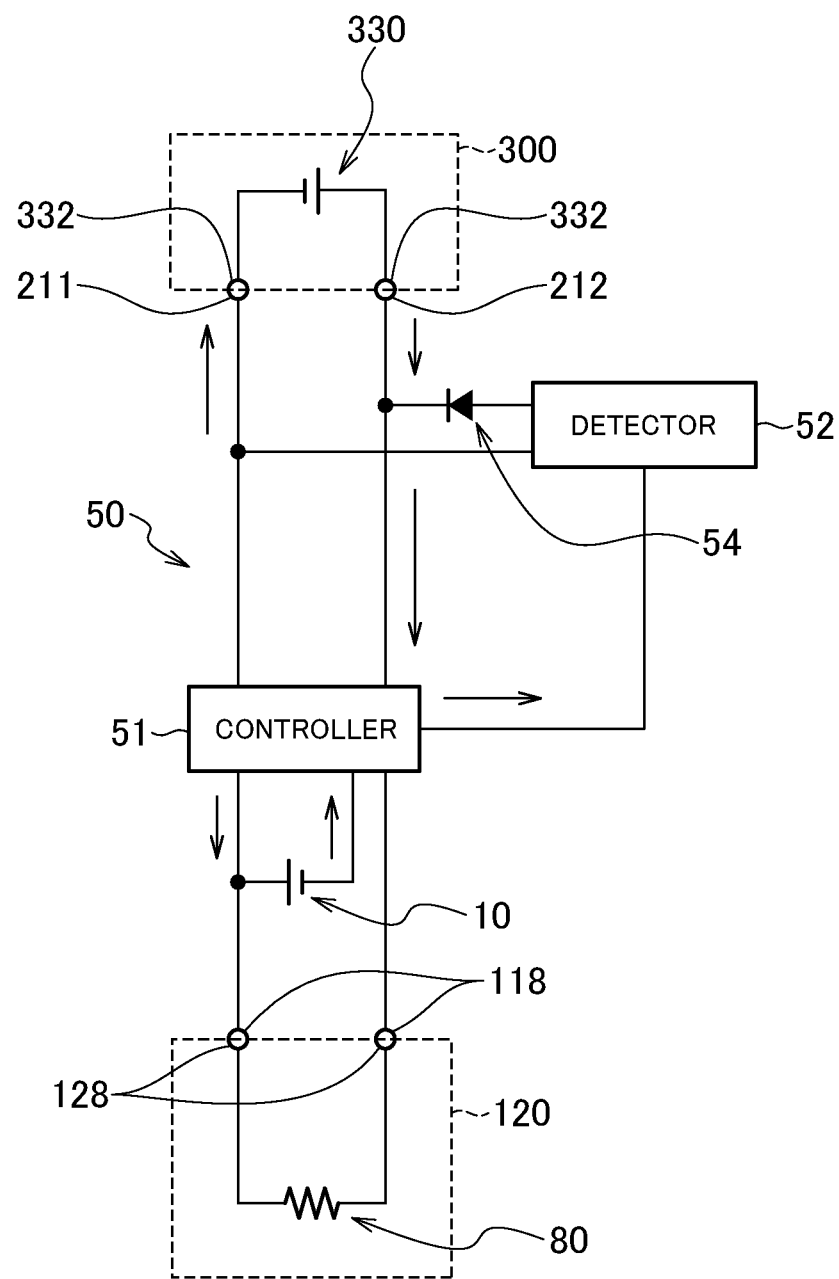
FIG. 12 is a schematic diagram of the flow of a current during charging in the control circuit according to the second embodiment.

FIG. 12 illustrates the flow of a current during charging in the control circuit 50. According to the second embodiment, when the non-combustion-type flavor inhaler 100 is inserted into a holder 320 of the charger 300, the first electrode 211 and the second electrode 212 of the power supply assembly 110 are electrically connected with the paired electrodes 332 on the charger 300 side. The charger 300 supplies a charging current to the power supply 10 of the power supply assembly 110 through the first electrode 211 and the second electrode 212. This arrangement can charge the power supply 10. Note that FIG. 12 illustrates, with an arrow, the direction of the flow of the current during charging.

According to the second embodiment, the control circuit 50 includes a rectifying element 54 that inhibits the charging current from flowing in the detector 52 when the charger 300 charges the power supply 10. The rectifying element 54 has an anode 55 and a cathode 56. The anode 55 is electrically connected with the detector 52. The cathode 56 is electrically connected with an electrode positive during the charging by the charger 300, from the first electrode 211 and the second electrode 212. This arrangement can prevent a large current during the charging from flowing in the detector 52.

Figure 13:
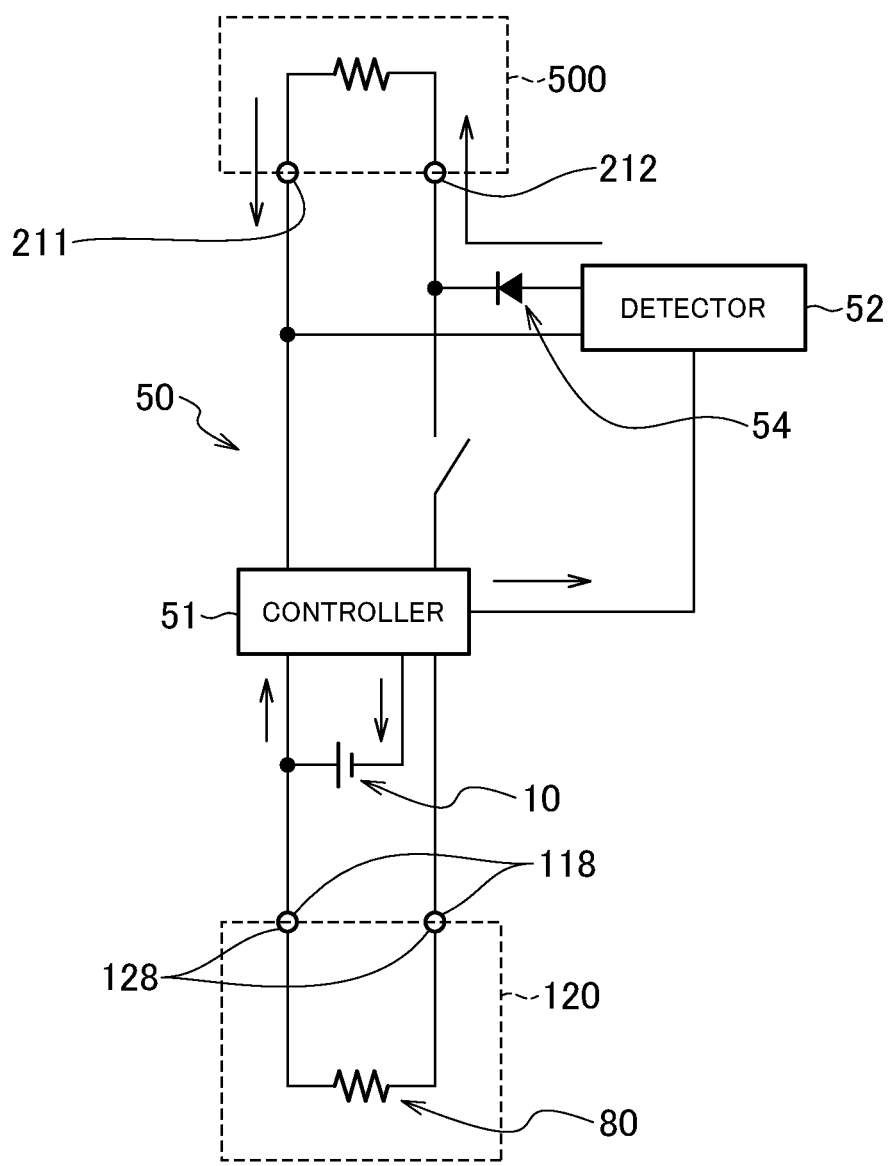
FIG. 13 is a schematic diagram of the flow of a current when a first electrode and a second electrode are in conduction in the control circuit according to the second embodiment.

FIG. 13 is a schematic diagram of the flow of a current when the first electrode 211 and the second electrode 212 are in conduction in the control circuit 50 according to the second embodiment. For example, when an external element 500, such as a finger of the user, touches the first electrode 211 and the second electrode 212 simultaneously, the first electrode 211 and the second electrode 212 are mutually in conduction as illustrated in FIG. 8. At this time, the power from the power supply 10 allows a predetermined current to flow between the first electrode 211 and the second electrode 212. The predetermined current flows in the opposite direction to that of the charging current, at the first electrode 211 and the second electrode 212. Note that FIG. 13 illustrates, with an arrow, the direction of the predetermined current when the first electrode 211 and the second electrode 212 are in conduction.

The control circuit 50 includes the detector 52 that detects the predetermined current in the opposite direction to the direction of the current (charging current) flowing through the second electrode 212 when the charger 300 charges the power supply 10, similarly to the first embodiment. The detector 52 may detect the presence or absence of the predetermined current that flows between the first electrode 211 and the second electrode 212. Instead of this, the detector 52 may be capable of detecting the difference between the direction of the current during charging and the direction of the current when the first electrode 211 and the second electrode 212 are in conduction. The detector 52 detects the predetermined current in the opposite direction to that of the charging current, so that the conduction between the first electrode 211 and the second electrode 212 can be detected. This arrangement can detect whether the user has touched the first electrode 211 and the second electrode 212 simultaneously.

Third Embodiment

A non-combustion-type flavor inhaler according to a third embodiment will be described below. Note that the same constituents as those of the non-combustion-type flavor inhaler according to the second embodiment, are denoted with the same reference signs, and thus the descriptions thereof will be omitted. Differences from the second embodiment will be mainly described below.

Figure 14:
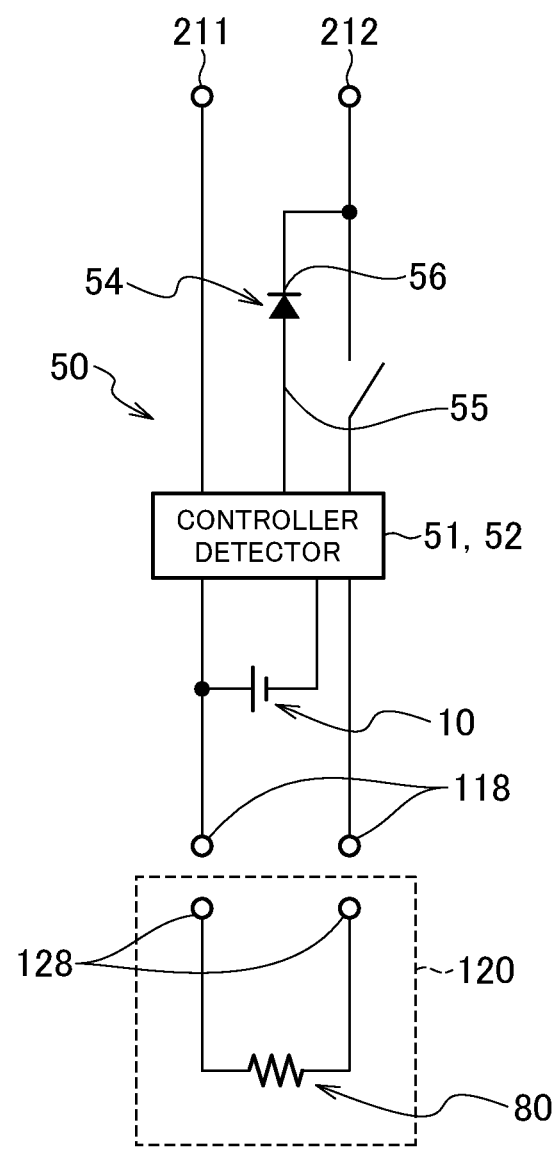
FIG. 14 is a schematic diagram of a control circuit according to a third embodiment.
Figure 15:
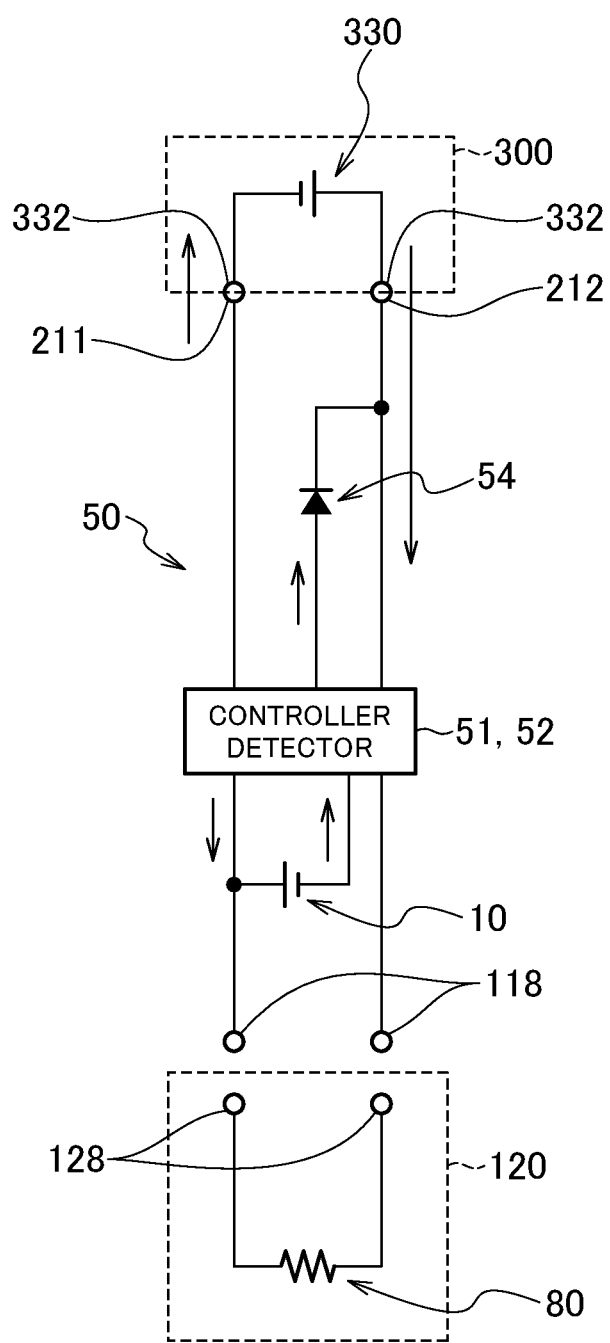
FIG. 15 is a schematic diagram of the flow of a current during charging in the control circuit according to the third embodiment.
Figure 16:
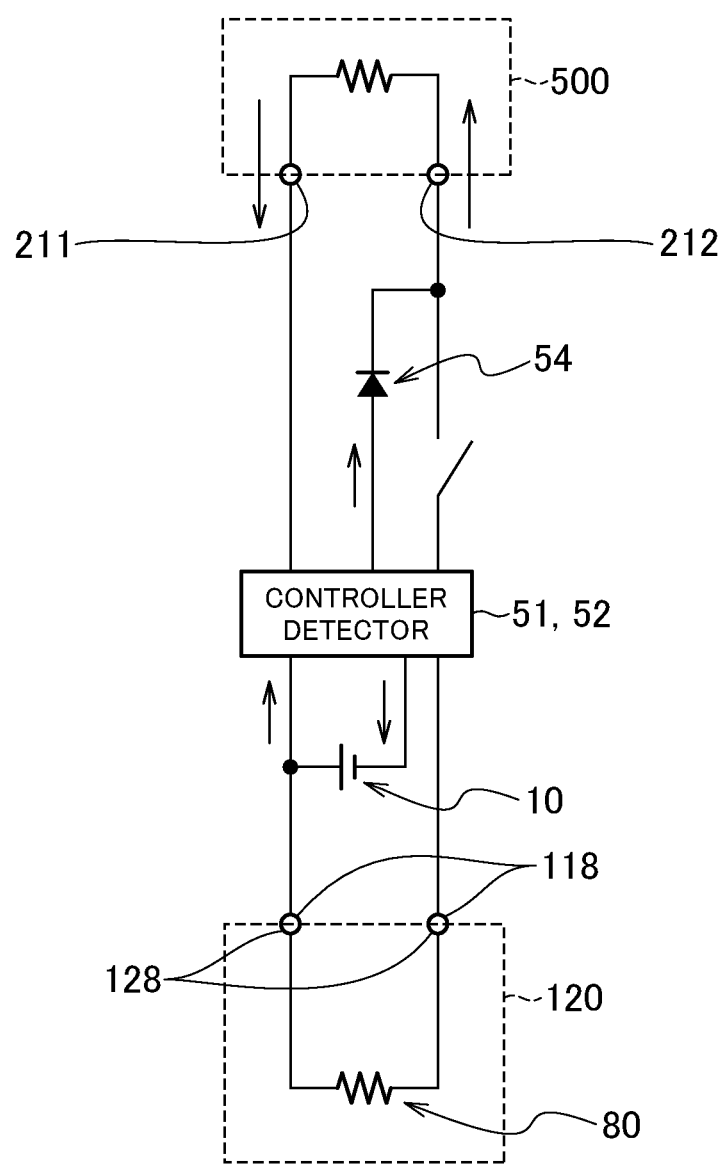
FIG. 16 is a schematic diagram of the flow of a current when a first electrode and a second electrode in conduction in the control circuit according to the third embodiment.

FIG. 14 is a schematic diagram of a control circuit according the third embodiment. FIG. 15 is a schematic diagram of the flow of a current during charging in the control circuit according to the third embodiment. FIG. 16 is a schematic diagram of the flow of a current when a first electrode and a second electrode are in conduction in the control circuit according to the third embodiment.

The control circuit 50 includes: a controller 51 for at least controlling power from a power supply 10 to an atomizer 80; and a detector 52 that detects a predetermined current in the opposite direction to that of a charging current. A rectifying element 54 is electrically connected with an electric wire extending from the first electrode 211 and an electric wire extending from the second electrode 212 through the controller 51 and the detector 52. The rectifying element 54 has an anode 55 and a cathode 56. The anode 55 is electrically connected with the detector 52. The cathode 56 is electrically connected with an electrode positive during charging by a charger 300, from the first electrode 211 and the second electrode 212. This arrangement can prevent a large current during the charging from flowing in the detector 52.

According to the third embodiment, the detector 52 can detect the predetermined current in the opposite direction to the direction of the current (charging current) flowing through the second electrode 212 when the charger 300 charges the power supply 10.

According to the third embodiment, the controller 51 and the detector 52 are mechanically disposed at the same location. Therefore, the controller 51 and the detector 52 are implementable on the same substrate, and thus are advantageous to miniaturization of the control circuit.

Fourth Embodiment

A non-combustion-type flavor inhalation system according to a fourth embodiment will be described below. Note that the same constituents as those of the non-combustion-type flavor inhalation system according to the first embodiment, are denoted with the same reference signs, and thus the description thereof will be omitted. Differences from the first embodiment will be mainly described below.

According to the fourth embodiment, the configuration of a non-combustion-type flavor inhaler 100 is the same as that of the non-combustion-type flavor inhaler 100 according to the first embodiment. According to the fourth embodiment, the configuration of a charger 300 is different from that according to the first embodiment.

Figure 17:
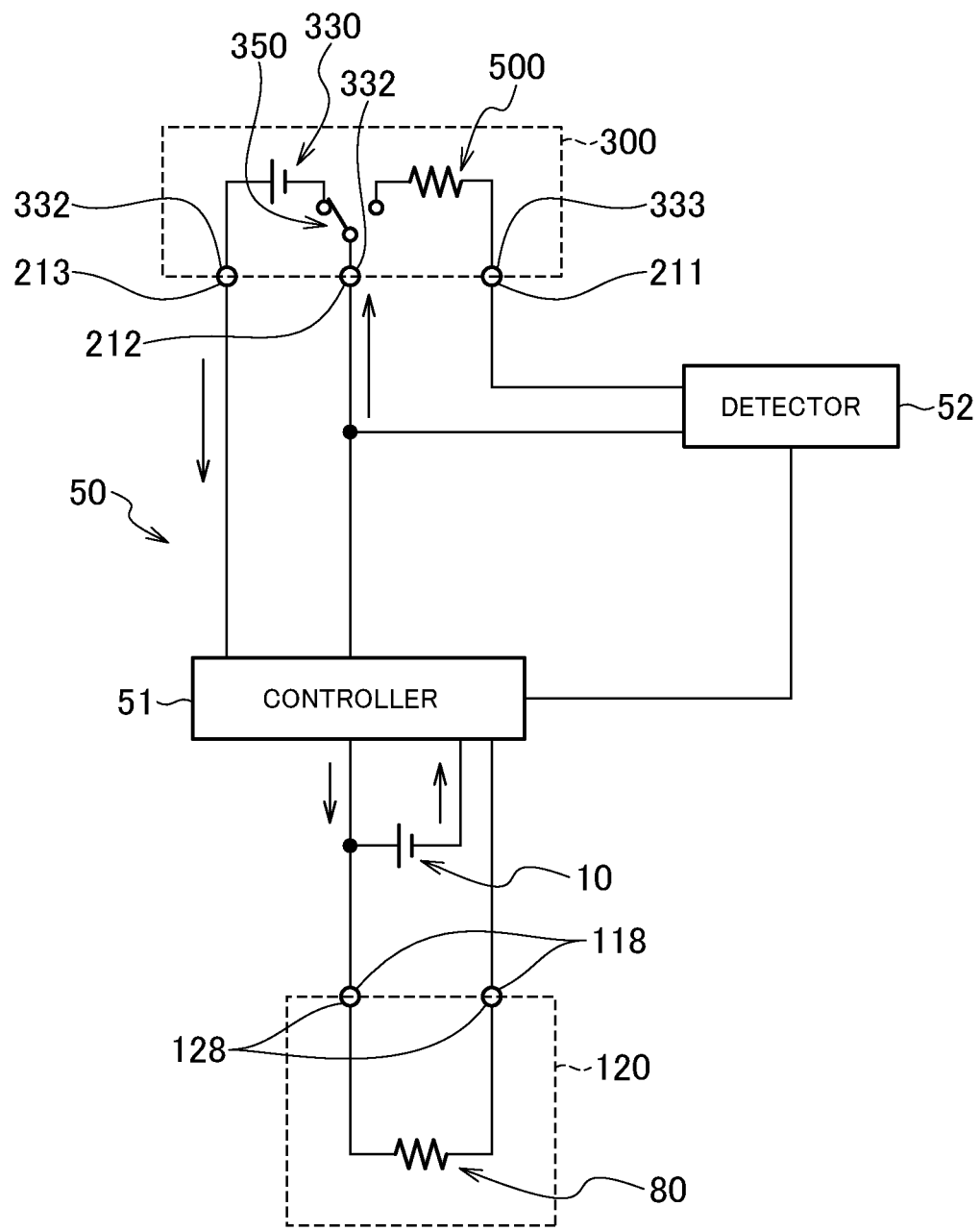
FIG. 17 is a schematic diagram of the flow of a current during charging in a control circuit according to a fourth embodiment.
Figure 18:
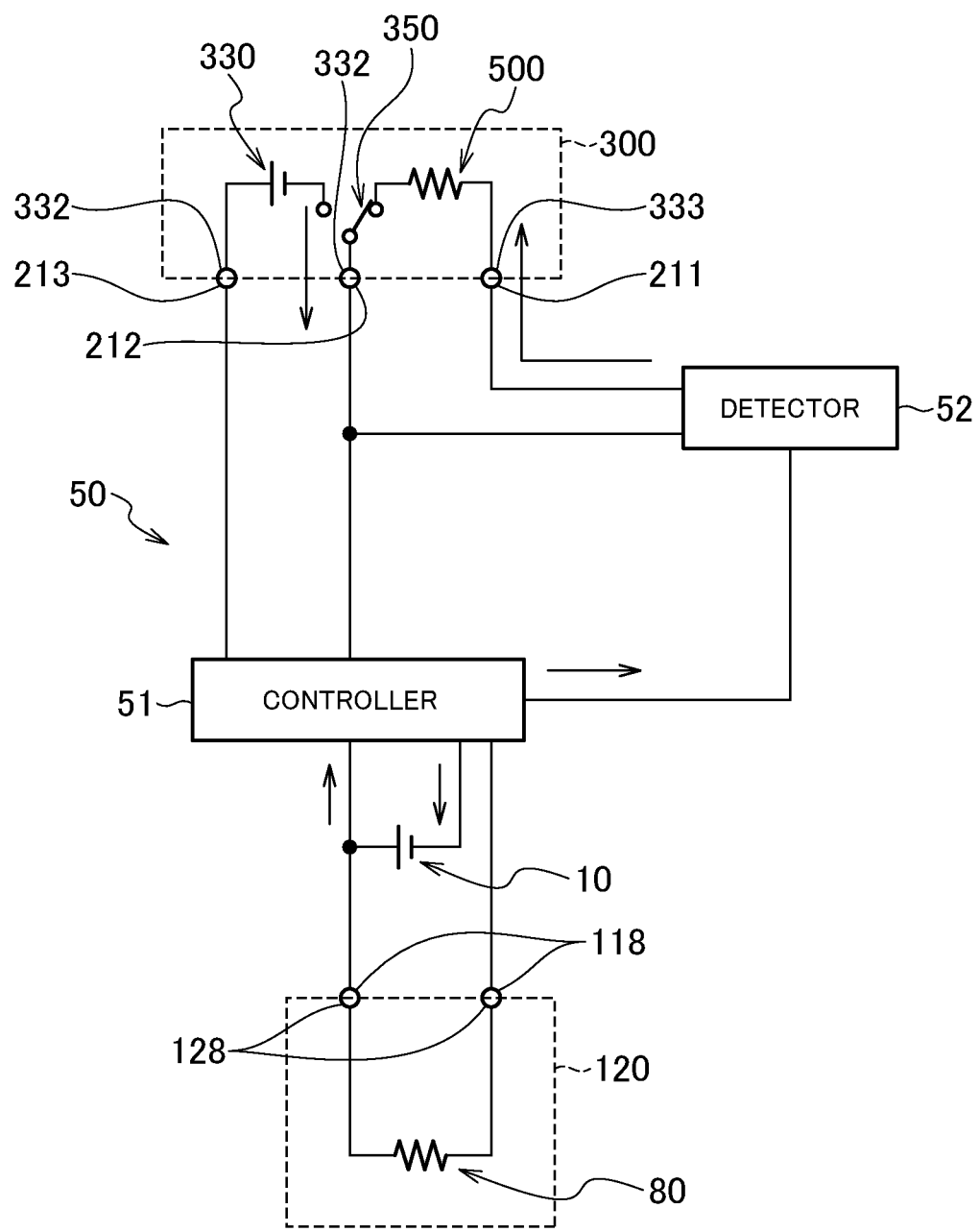
FIG. 18 is a schematic diagram of the flow of a current when a first electrode and a second electrode are in conduction in the control circuit according to the fourth embodiment.

FIG. 17 is a schematic diagram of the flow of a current during charging in a control circuit according to the fourth embodiment. FIG. 18 is a schematic diagram of the flow of a current when a first electrode and a second electrode are in conduction in the control circuit according to the fourth embodiment. The configuration of the control circuit 50 of the non-combustion-type flavor inhaler 100 is similar to that according to the first embodiment.

The charger 300 includes a different electrode 333 in addition to paired electrodes 332 for charging. When the non-combustion-type flavor inhaler 100 is inserted into a holder of the charger 300, the second electrode 212 and a third electrode 213 of a power supply assembly 110 are electrically connected with the paired electrodes 332 for charging. Meanwhile, the first electrode 211 that does not contribute to charging, is electrically connected with the electrode 333 of the charger 300.

According to the fourth embodiment, the charger 300 includes switching means 350 capable of switching one of the paired electrodes 332 for charging and the electrode 333 between a conduction state and a non-conduction state. The switching means 350 can adopt, for example, a switch. The switch is switchable with, for example, a push button provided to a case 310 of the charger 300.

As illustrated in FIG. 17, during charging, the one of the paired electrodes 332 for charging and the electrode 333 are in the non-conduction state. A secondary battery 330 of the charger is electrically connected with the second electrode 212 and the third electrode 213 through the second electrode 212 and the third electrode 213. Therefore, the power supply 10 can be charged.

For example, pressing the push button provided to the charger 300 allows the one of the paired electrodes 332 for charging and the electrode 333 to be switched to the conduction state. This arrangement allows the first electrode 211 and the second electrode 212 to be switched into conduction, as illustrated in FIG. 18. At this time, a predetermined current in the opposite direction to that of a charging current, flows at least at the second electrode 212, similarly to the first embodiment. A detector 52 of the control circuit 50 can detect the predetermined current in the opposite direction to that of the charging current. This arrangement can detect the conduction between the first electrode 211 and the second electrode 212, with the charger 300. The detection of the conduction between the first electrode 211 and the second electrode 212 can be used for user authentication or mode switching operation, as described in the first embodiment.

As illustrated in FIG. 18, when the first electrode 211 and the second electrode 212 are in conduction, the secondary battery 330 of the charger is out of conduction with the power supply 10. This arrangement cancels the charging to the power supply 10 with the first electrode 211 and the second electrode 212 in conduction.

Fifth Embodiment

A non-combustion-type flavor inhaler according to a fifth embodiment will be described below. Note that the same constituents as those of the non-combustion-type flavor inhaler according to the first embodiment, are denoted with the same reference signs, and thus the descriptions thereof will be omitted. Differences from the first embodiment will be mainly described below.

Figure 19:
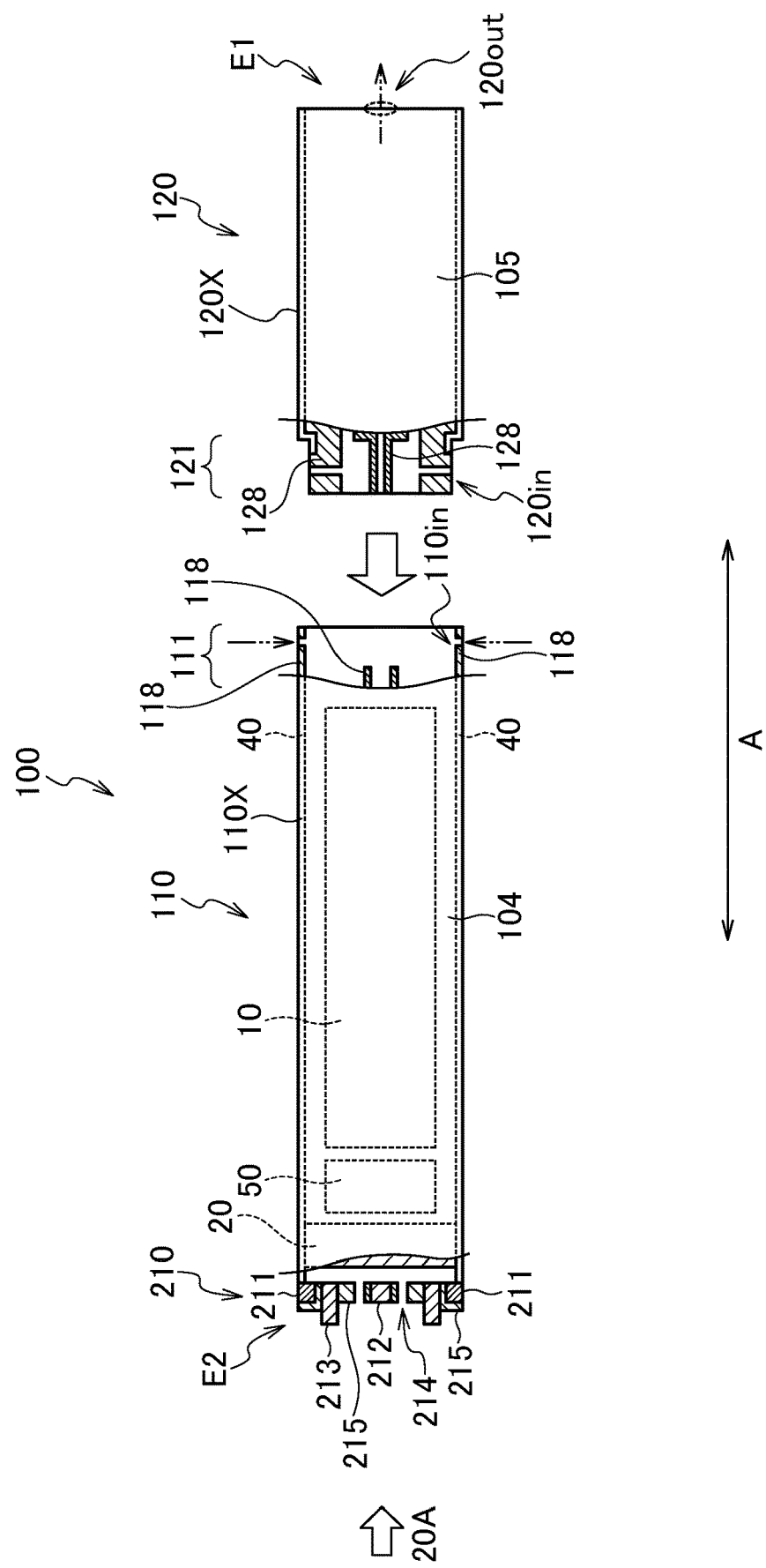
FIG. 19 is a view of a non-combustion-type flavor inhaler according to a fifth embodiment.
Figure 20:
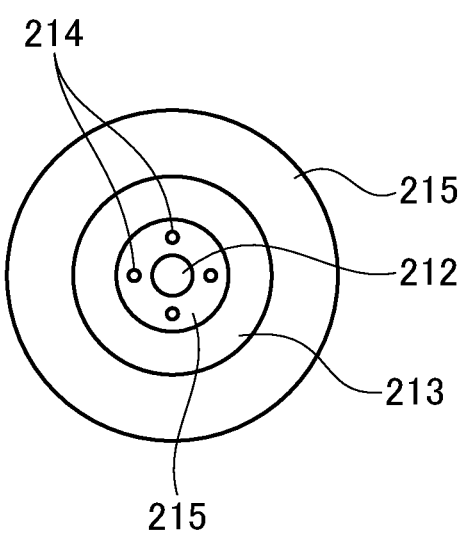
FIG. 20 is a plan view of a power supply assembly viewed in the direction of an arrow 20A of FIG. 19.

FIG. 19 is a view of the non-combustion-type flavor inhaler according to the fifth embodiment. FIG. 20 is a plan view of a power supply assembly viewed in the direction of an arrow 20A of FIG. 19. The fifth embodiment is different from the first embodiment regarding the position of an opening 214 provided to the power supply assembly 110, the opening 214 being in communication with the atmosphere. Specifically, the opening 214 is provided to the end face on the non-mouthpiece end E2 side of a first case 110X instead of the lateral face of the first case 110X. More specifically, an insulating member 215 insulating a second electrode 212 and a third electrode 213, has the opening 214 formed.

According to the present embodiment, the non-combustion-type flavor inhaler may include the sensor 20 described in the first embodiment. The sensor 20 can detect an inhalation action of a user.

According to the present embodiment, the opening 214 in communication with a second cavity 106 is provided to the end face on the non-mouthpiece end E2 side of the first case 110X. Thus, at the same time a finger of the user is put onto the second electrode 212 at a recess position on the end face on the non-mouthpiece end E2 side of the first case 110X, the finger of the user blocks the opening 214. The block causes an air flow, so that the internal pressure of the second cavity 106 rises. In other words, the sensor 20 can detect an action in which the user touches the second electrode 212.

When a control circuit 50 detects a predetermined current in the opposite direction to the direction of a current flowing through the second electrode 212 when the charger 300 charges a power supply 10 and additionally the sensor 20 detects the action in which the user touches the second electrode 212, the control circuit 50 may perform the predetermined control described above.

Other Embodiments

The present invention has been described in the embodiments, but it should not be understood that the invention is limited to the descriptions and the drawings included in part of this disclosure. The disclosure clarifies various alternative embodiments, examples, and investment techniques, for persons skilled in the art.

For example, the rectifying element 54 described in the second embodiment may be applied to the control circuit 50 according to the first embodiment.

The embodiment has exemplified the tobacco source 131 as a flavor source. However, the embodiment is not limited to this. The flavor source does not necessarily contain tobacco material. Furthermore, the non-combustion-type flavor inhaler 100 does not necessarily include the flavor source, but an inhalant flavor ingredient may be added to the aerosol source.

The embodiment has exemplified that the reservoir 60 that stores the aerosol source is the porous body. However, the embodiment is not limited to this. The reservoir 60 may be a tank that houses a liquid aerosol source.

The embodiment has exemplified that the non-combustion-type flavor inhaler 100 includes the capsule unit 130. However, the embodiment is not limited to this. For example, the non-combustion-type flavor inhaler 100 may include a cartridge including a flavor source.

According to the embodiment, at least one of the first electrode 211 and the second electrode 212 is electrically connectable to the charger 300 for charging the power supply 10. In addition to this, the first paired electrodes 118 of the power supply assembly 110, namely, the paired electrodes for electrical connection with the atomizer 80 may be electrically connectable to the charger 300.

According to the embodiment, the power supply assembly 110 and the atomization assembly 120 are capable of screwing mutually with the spiral groove and the spiral protrusion. However, the embodiment is not limited to this. Engagement between a claw rib formed on the first case 110X of the power supply assembly 110 and a recess formed on the second case 120X of the atomization assembly 120 may enable the power supply assembly 110 and the atomization assembly 120 to engage with each other.

According to the embodiment, the atomizer 80 is controlled on the basis of the output value of the sensor 20 that detects the inhalation action of the user. Instead of this, pressing of a push button by the user may allow the atomizer 80 to be controlled, namely, the aerosol source to be atomized.

A mouthpiece to be held in the user' mouth, may be detachably attached on the mouthpiece end E1 side of the atomization assembly 120. Instead of this, the mouthpiece may be integrally formed with the atomization assembly 120. In this case, the mouthpiece and the atomization assembly 120 are to be replaced as one set.

The invention claimed is:

1. A non-combustion-type flavor inhaler comprising:
an atomization assembly including an atomizer configured to atomize an aerosol source without combustion; and
a power supply assembly including a power supply for supplying power to the atomizer,
wherein the power supply assembly includes:
paired electrodes for electrical connection with the atomizer; and
a first electrode and a second electrode electrically connected with the power supply,
wherein at least one of the first electrode and the second electrode is electrically connectable to a charger for charging the power supply,
wherein the non-combustion-type flavor inhaler is provided with a control circuit configured to detect an opposite current that flows through the at least one of the first electrode and the second electrode in a direction opposite to a charging current, the charging current flowing through the first electrode or the second electrode when the charger charges the power supply, and
wherein the control circuit is configured to perform a predetermined control if a number of times where the opposite current is detected within a predetermined period exceeds a predetermined threshold that is larger than one.

2. The non-combustion-type flavor inhaler according to claim 1, wherein the opposite current is generated from the power supply.

3. The non-combustion-type flavor inhaler according to claim 1, wherein
the power supply assembly includes a first case housing the power supply, the first case including first paired electrodes being the paired electrodes,
the atomization assembly includes a second case housing the atomizer, the second case including second paired electrodes, the second case being detachably attachable to the first case, and
the first paired electrodes and the second paired electrodes are configured to electrically connect together when the first paired electrodes and the second paired electrodes are in contact with each other.

4. The non-combustion-type flavor inhaler according to claim 3, wherein at least one of the first case and the second case includes an engagement for engaging the first case and the second case together.

5. The non-combustion-type flavor inhaler according to claim 3, wherein, with the first paired electrodes and the second paired electrodes electrically connected together, the first electrode and the second electrode are disposed at positions at which an external element different from constituent elements of the non-combustion-type flavor inhaler enables the first electrode and the second electrode to be in conduction.

6. The non-combustion-type flavor inhaler according to claim 3, wherein, with the first paired electrodes and the second paired electrodes electrically connected together, each of the first electrode and the second electrode have a portion exposed on a surface of the first case.

7. The non-combustion-type flavor inhaler according to claim 6, wherein an exposed portion of the first electrode and an exposed portion of the second electrode are disposed on faces facing mutually different directions in the first case.

8. The non-combustion-type flavor inhaler according to claim 6, wherein an exposed portion of the first electrode and an exposed portion of the second electrode are disposed on faces facing identical directions in the first case, and
a difference in level is provided between an end face of the exposed portion of the first electrode and an end face of the exposed portion of the second electrode.

9. The non-combustion-type flavor inhaler according to claim 3, wherein, with the first paired electrodes and the second paired electrodes electrically connected together, the first paired electrodes are disposed at positions at which conduction of an external element different from constituent elements of the non-combustion-type flavor inhaler, is not allowed between the first paired electrodes.

10. The non-combustion-type flavor inhaler according to claim 9, wherein, with the first paired electrodes and the second paired electrodes electrically connected together, at least one of the first paired electrodes is not exposed on a surface of the non-combustion-type flavor inhaler.

11. The non-combustion-type flavor inhaler according to claim 1, wherein both of the first electrode and the second electrode are electrically connectable to the charger for charging the power supply, and
the power supply is configured to be charged by the charger through the first electrode and the second electrode.

12. The non-combustion-type flavor inhaler according to claim 1, wherein the control circuit includes:
a detector configured to detect the opposite current; and
a rectifying element configured to prevent a charging current from flowing in the detector.

13. The non-combustion-type flavor inhaler according to claim 12, wherein the rectifying element includes an anode and a cathode,
the anode is electrically connected with the detector, and
the cathode is electrically connected with an electrode positive during the charging by the charger, among the first electrode and the second electrode.

14. The non-combustion-type flavor inhaler according to claim 1, wherein the power supply is configured to be charged by the charger through one of the first electrode and the second electrode.

15. The non-combustion-type flavor inhaler according to claim 1, wherein the power supply assembly includes a third electrode different from the first electrode and the second electrode, and
wherein a charging current is configured to be supplied from the charger to the power supply through the third electrode and only one of the first electrode and the second electrode.

16. The non-combustion-type flavor inhaler according to claim 15, wherein
an electrode that does not contribute to supply of the charging current supplied from the charger to the power supply, among the first electrode and the second electrode is:
provided at a position at which the electrode is physically out of contact with the charger;
physically in contact with the charger through an insulator preventing electrical connection with the charger; or
electrically connected with the charger and does not contribute to the supply of the charging current from the charger to the power supply.

17. The non-combustion-type flavor inhaler according to claim 1, wherein the control circuit is configured to control a power from the power supply to the atomizer.

18. The non-combustion-type flavor inhaler according to claim 17, wherein the control circuit detects whether the power supply is being charged, and the control circuit does not perform the predetermined control regardless of a detected result of the opposite current when detecting the charging of the power supply.

19. A non-combustion-type flavor inhalation system comprising:

the non-combustion-type flavor inhaler according to claim 1; and a charger detachably attachable to the non-combustion-type flavor inhaler, the charger being capable of supplying a charging current to the non-combustion-type flavor inhaler.

20. The non-combustion-type flavor inhalation system according to claim 19, wherein the charger includes third paired electrodes for electrical connection between the charger and the non-combustion-type flavor inhaler, the third paired electrodes are electrically connected with the first electrode and the second electrode when the charger and the non-combustion-type flavor inhaler are attached to each other, and the opposite current is supplied to the control circuit by a conduction between the electrodes included in the third paired electrodes.

21. The non-combustion-type flavor inhalation system according to claim 20, wherein the charger includes switching means capable of switching between a conduction state and a non-conduction state of the electrodes included in the third paired electrodes.

22. A power supply assembly comprising:

a power supply for supplying power to an atomizer configured to atomize an aerosol source without combustion;

paired electrodes for electrical connection with the atomizer;

a first electrode and a second electrode electrically connected with the power supply, wherein at least one of the first electrode and the second electrode is electrically connectable to a charger for charging the power supply; and a controller configured to detect an opposite current that flows through the at least one of the first electrode and the second electrode in a direction opposite to a charging current flowing through the first electrode or the second electrode when the charger charges the power supply, wherein the controller is configured to perform a predetermined control if a number of times where the opposite current is detected within a predetermined period exceeds a predetermined threshold that is larger than one.

* * * * *